United States Patent

Brough et al.

(10) Patent No.: US 6,958,350 B2
(45) Date of Patent: Oct. 25, 2005

(54) CHEMICAL COMPOUNDS

(75) Inventors: Stephen Brough, Loughborough (GB); Thomas McInally, Loughborough (GB); Matthew Perry, Loughborough (GB); Brian Springthorpe, Loughborough (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 10/468,179

(22) PCT Filed: Feb. 18, 2002

(86) PCT No.: PCT/SE02/00269

§ 371 (c)(1),
(2), (4) Date: Aug. 18, 2003

(87) PCT Pub. No.: WO02/066460

PCT Pub. Date: Aug. 29, 2002

(65) Prior Publication Data

US 2004/0102483 A1 May 27, 2004

(30) Foreign Application Priority Data

Feb. 19, 2001 (GB) .............................. 0104050

(51) Int. Cl.⁷ ................. A61K 31/454; A61K 31/4535; C07D 401/14; C07D 413/12; C07D 417/12
(52) U.S. Cl. ...................... 514/318; 514/321; 514/326; 546/209; 546/208; 546/207; 546/210; 546/211; 546/194
(58) Field of Search ................................ 546/209, 210, 546/211, 208, 207, 194; 514/318, 321, 326

(56) References Cited

U.S. PATENT DOCUMENTS

| | | | |
|---|---|---|---|
| 3,203,992 A | 8/1965 | Kunz et al. | |
| 3,577,432 A | 5/1971 | Helsley et al. | |
| 3,755,584 A | 8/1973 | Plotnikoff et al. | |
| 3,818,017 A | 6/1974 | Janssen et al. | |
| 3,894,030 A | 7/1975 | Janssen et al. | |
| 4,029,801 A | 6/1977 | Cavalla et al. | |
| 4,105,666 A | 8/1978 | Ward | |
| 4,105,771 A | 8/1978 | Archibald et al. | |
| 4,166,119 A | 8/1979 | Effland et al. | |
| 4,246,267 A | 1/1981 | Vincent et al. | |
| 4,264,613 A | 4/1981 | Regnier et al. | |
| 4,338,323 A | 7/1982 | Regnier et al. | |
| 5,576,321 A | 11/1996 | Krushinski, Jr. et al. | |
| 5,614,523 A | 3/1997 | Audia et al. | |
| 5,614,533 A | 3/1997 | Anderson et al. | |
| 5,627,196 A | 5/1997 | Audia et al. | |
| 5,688,960 A | 11/1997 | Shankar | |
| 5,696,267 A | 12/1997 | Reichard et al. | |
| 5,741,789 A | 4/1998 | Hibschman et al. | |
| 5,789,402 A | 8/1998 | Audia et al. | |
| 5,840,725 A | 11/1998 | Reichard et al. | |

FOREIGN PATENT DOCUMENTS

| | | |
|---|---|---|
| DE | 37 23 568 | 1/1989 |
| DE | 197 03 131 | 7/1998 |
| DE | 197 55 268 | 6/1999 |
| EP | 0 095 454 | 11/1983 |
| EP | 0 128 007 | 12/1984 |
| EP | 0 354 568 A2 | 2/1990 |
| EP | 0 407 217 A1 | 1/1991 |
| EP | 0 445 862 B1 | 9/1991 |
| EP | 0 457 686 B1 | 11/1991 |
| EP | 0 496 691 | 7/1992 |
| EP | 0 587 311 | 3/1994 |
| EP | 0 625 507 B1 | 11/1994 |
| EP | 0 643 057 A1 | 3/1995 |
| EP | 0 722 941 | 7/1996 |
| EP | 0 903 349 | 3/1999 |
| EP | 1 013 276 A1 | 6/2000 |
| FR | 2 190 430 | 2/1974 |
| GB | 1368012 | 9/1974 |
| GB | 1 404 868 | 9/1975 |
| GB | 1 425 354 | 2/1976 |
| GB | 1 532 671 | 11/1978 |
| GB | 1 538 542 | 1/1979 |
| GB | 1 544 191 | 4/1979 |
| JP | 63-264525 | 11/1988 |
| JP | 10259176 | 9/1998 |
| WO | WO 92/15579 | 9/1992 |
| WO | WO 93/13083 | 7/1993 |
| WO | WO 93/25528 | 12/1993 |
| WO | WO 94/27967 | 12/1994 |
| WO | WO 95/11880 | 5/1995 |
| WO | WO 96/26205 | 8/1996 |
| WO | WO 96/34857 | 11/1996 |
| WO | WO 96/39386 | 12/1996 |
| WO | WO 97/10207 | 3/1997 |
| WO | WO 97/19060 | 5/1997 |
| WO | WO 97/23458 | 7/1997 |
| WO | WO 97/42956 | 11/1997 |

(Continued)

OTHER PUBLICATIONS

Rollins BJ. Blood. 1997, 90(3): 909–928.*
U.S. Appl. No. 10/204,754, filed Aug. 23 2002, Hansen et al.
U.S. Appl. No. 10/204,789, filed Aug. 23, 2002, Hansen et al.
U.S. Appl. No. 10/204,790, filed Aug. 23, 2002, Bodkin et al.
U.S. Appl. No. 10/311,667, filed Dec. 17, 2002, Eriksson et al.

(Continued)

Primary Examiner—Evelyn Mei Huang
(74) Attorney, Agent, or Firm—Fish & Richardson P.C.

(57) ABSTRACT

The invention provides a compound of formula (I): wherein $R^1$, $R^2$, $R^3$, $R^4$, $R^5$, N, X and Y are as defined in the specification, processes, for their preparation, pharmaceutical compositions containing them, and their use in therapy, especially for the treatment of chemokine receptor related diseases and conditions.

8 Claims, No Drawings

FOREIGN PATENT DOCUMENTS

| WO | WO 97/47299 | | 12/1997 |
|---|---|---|---|
| WO | WO 98/02151 | | 1/1998 |
| WO | WO 98/08826 | | 3/1998 |
| WO | WO 98/31364 | | 7/1998 |
| WO | WO 98/31366 | | 7/1998 |
| WO | WO 98/32442 | | 7/1998 |
| WO | WO 98/51311 | | 11/1998 |
| WO | WO 99/04794 | | 2/1999 |
| WO | WO 99/25686 | | 5/1999 |
| WO | WO 99/27928 | | 6/1999 |
| WO | WO 99/27929 | | 6/1999 |
| WO | WO 99/28314 | | 6/1999 |
| WO | WO 99/31092 | | 6/1999 |
| WO | WO 99/37304 | | 7/1999 |
| WO | WO 99/37619 | | 7/1999 |
| WO | WO 99/38514 | | 8/1999 |
| WO | WO 99/64394 | | 12/1999 |
| WO | WO 99/65895 | | 12/1999 |
| WO | WO 00/08013 | | 2/2000 |
| WO | WO 00/21948 | | 4/2000 |
| WO | WO 00/21952 | | 4/2000 |
| WO | WO 00/23076 | | 4/2000 |
| WO | WO 00/35449 | | 6/2000 |
| WO | WO 00/35451 | | 6/2000 |
| WO | WO 00/39108 | | 7/2000 |
| WO | WO 00/53600 | | 9/2000 |
| WO | WO 00/58305 | | 10/2000 |
| WO | WO 00/61559 | | 10/2000 |
| WO | WO 00/69820 | | 11/2000 |
| WO | WO 00/76513 | A1 | 12/2000 |
| WO | WO 00/76973 | A1 | 12/2000 |
| WO | WO 01/14333 | A1 | 3/2001 |
| WO | WO 01/43744 | | 6/2001 |
| WO | WO 01/44227 | | 6/2001 |
| WO | WO 01/87839 | A1 | 11/2001 |
| WO | WO 01/92227 | A1 | 12/2001 |
| WO | WO 02/070479 | | 9/2002 |
| WO | WO 02/076948 | | 10/2002 |
| WO | WO 02/079156 | | 10/2002 |
| WO | WO 02/079256 | | 10/2002 |
| WO | WO 03/042177 | | 5/2003 |
| WO | WO 03/042178 | | 5/2003 |
| WO | WO 03/042205 | | 5/2003 |

OTHER PUBLICATIONS

U.S. Appl. No. 10/311,841, filed Dec. 17, 2002, Eriksson et al.

U.S. Appl. No. 10/472,017, filed Sep. 19, 2003, Eriksson et al.

U.S. Appl. No. 10/472,412, filed Sep. 16, 2003, Eriksson et al.

Archibald et al., "Antiinflammatory 4–acylaminopiperidines", CAPLUS77:34355 (1972).

Cattanach et al., "Studies in the Indole Series. Part IV. Tetrahydro–1H–pyrido[4, 3–b]–indoles as Serotonin Antagonists", J. Chem. Soc. C. 10:1235–1243 (1968).

Cohen et al., "Cytokine function: A study in biologic diversity", CAPLUS 125:31527 (1996).

Friebe et al., "Piperidinopropyl derivatives and pharmaceutical compositions containing them", CAPLUS 94:103172 (1981).

Hesselgesser et al., "Identification and Characterization of Small Molecule Functional Antagonists of the CCR1 Chemokine Receptor", J. Biol. Chem. 273(25):15687–15692 (1998).

Howard et al., "Chemokines: progress toward identifying molecular targets for therapeutic agents", Trends in Biotechnology 14:46–51 (1996).

Manabu Hori Kim D. Janda, "A Soluble Polymer Approach to the "Fishing Out" Principle: Synthesis and Purification of β–Amino Alcohols", J. Org. Chem. 63:889–894 (1998).

Komai et al., "Structure–Activity Relationships of HIV–1 PR Inhibitors Containing AHPBA–II. Modification of Pyrrolidine Ring at P1' Proline", Bioorganic & Medicinal Chemistry 4(8):1365–1377 (1996).

Leclerc et al., "Derivatives Related to Betaxolol with I–and J–Adrenergic Activities", Arzneim.–Forsch/Drug. Res. 35(11):1357–1367 (1985).

Meurer et al., "Discovery of potent human CCR5 antagonists for the treatment of HIV–1 infection—II.", CAPLUS 2000:331722 (2000).

Navas III et al., "The Design and Synthesis of a Hapten for 1192U90, A Potential Atypical Antipsychotic Agent", Synthetic Communications 26(7):1411–1421 (1996).

Payard et al., "N–Aminomethylated Derivatives of Some Hydroxamine Acids as Anti–Inflammatories", Eur. J. Med. Chem. pp. 1–10 (1975).

Rubini et al., "Synthesis of Isosteric Methylene–Oxy Pseudodipeptide Analogues as Novel Amide Bond Surrogate Units", Tetrahedron 42(21):6039–6045 (1986).

STN Int'l, CAPLUS 1968.402884.

Timmermans et al., "Hypotensive Properties of Benzodioxane Derivatives Structurally Related to R 28935. Comparison of Activity with some Receptor Affinities", Arch. int. Pharmacodyn. 255:321–334 (1982).

Wright et al., "Discovery of Selective Dopamine D4 Receptor Antagonists: 1–Aryloxy–3–(4–Aryloxypiperidinyl)–2–Propanols", Bioorganic & Medicinal Chemistry Letters 7(11):1377–1380 (1997).

Archibald et al., "Antiinflammatory 4–acylaminopiperidines", CAPLUS 77:34355 (1972).

CAPLUS accession No. 1978:22640, document No. 88:22640, Yoshitomi Pharmaceutical Industries Ltd.: "Urea and thiourea derivatives" & JP, A2, 52085174, 19770715.

CAPLUS, accession No. 1990:558675, document No. 113:158675, Yoshitomi Pharmaceutical Industries, Ltd.: "Dihydroxycinnamic acid amide derivatives and their pharmaceutical compositions for enhancement of nerve growth factor (NGF) production" & JP, A2, 02104568, 19900417.

Derwent Abstract 54050W/33 corresponding to Belgium Application BE 826994.

Derwent Abstract 2000–339628/29 corresponding to PCT Application WO 00/23437 A1.

Derwent Abstract 96–136185/14 corresponding to Japanese Patent Application JP 08026999.

Derwent Abstract 96–136186/14 corresponding to Japanese Patent Application JP 08027000–A.

Derwent Abstract 96–136187/14 corresponding to Japanese Patent Application JP 08027001–A.

Derwent Abstract 99–040684/04 corresponding to Japanese Patent Application JP 10298180–A/2.

Emonds–Alt et al., "Pharmacological Profile and Chemical Synthesis of SR 48968, a Non–Peptide Antagonist of the Neurokinin A ($NK_2$) Receptor", Bioorganic & Medicinal Chemistry Letters 3(5):925–930 (1993).

Gerard, "Chemokine Receptors and Ligand Specificity: Understanding the Enigma", Chemokines and Cancer vol. 13, No. 72 (C–570):21–31, Feb. 17, 1999.

Granata et al., "Secretory phospholipases a(2) as multivalent mediators of inflammatory and allergic disorders", PubMed Abstract 12876405, also cited as *Int Arch Allergy Immunol.* 131(3):153–163 (2003).

Lawrence et al., "Automated Synthesis and Purification of Amides: Exploitation of Automated Solid Phase Extraction in Organic Synthesis", *Synthesis* 553–558, see table 1 (May 1997).

Mensonides–Harsema et al., "Synthesis and in Vitro and in Vivo Functional Studies of Ortho–Substituted Phenylpiperazine and N–Substituted 4–N–(o–Methoxyphenyl)aminopiperidine Analogues of WAY100635", *J. Med. Chem.* 43:432–439 (2000).

Naya et al., "Design, Synthesis, and Discovery of a Novel CCRI Antagonist", *J.Med. Chem.* 44:1429–1435 (2001).

Ng et al., "Discovery of Novel Non–Peptide CCR1 Receptor Antagonists", *Journal of Medicinal Chemistry* 42:4680–4694 (1999).

Scott et al., "Secreted phospholipase A(2) enzymes as therapeutic targets", PubMed Abstract 12783578, also cited as *Expert Opin Ther Targets* 7(3):427–40 (2003).

Srulevitch et al., "4–Phenylamidopiperidines: synthesis, pharmacological testing and SAR analysis", *Acta Pharm. Jugosl.* 41:89–106 (1991).

Srulevitch et al., "Design, Synthesis and SAR of Analgesics", QSAR: Quantitative Structure–Activity Relationships in Drug Design, pp. 377–381 (1989).

Stefano et al., "Human neutrophil and macrophage chemokinesis induced by cardiopulmonary bypass: Loss of DAME and IL–1 chemotaxis", *Journal of Neuroimmunology* 47:189–198 (1993).

Wade et al., "Application of Base Cleavable Safety Catch Linkers to Solid Phase Library Production", *J. Comb. Chem.* 2:266–275, see p. 269 scheme 3 and table 4, compounds 32 a–m (2000).

\* cited by examiner

CHEMICAL COMPOUNDS

CROSS-REFERENCE TO RELATED APPLICATIONS

This application is the national phase application under 35 U.S.C. § 371 of PCT International Application No. PCT/SE2002/00269, filed Feb. 18, 2002, which claims priority to Great Britain Application Serial No. 0104050.0, February Jul. 19, 2001.

The present invention relates to substituted piperidine compounds, processes for their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemoline superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

The present invention provides a compound of formula (I):

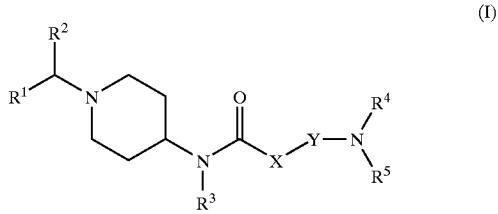

wherein:
$R^1$ is phenyl which is optionally substituted by halogen, $C_{1-4}$ alkyl, $C_{1-4}$ haloalkyl, $C_{1-4}$ alkoxy, $C_{1-4}$ haloalkoxy, nitro or cyano;
$R^2$, $R^3$ and $R^4$ are, independently, hydrogen or $C_{1-4}$ alkyl;
$R^5$ is $C_{1-6}$ alkyl, aryl, heteroaryl, aryl($C_{1-4}$)alkyl, heteroaryl ($C_{1-4}$)alkyl or $C_{3-8}$ cycloalkyl;
wherein the aryl and heteroaryl moieties of $R^5$ are optionally substituted by halogen, $C_{1-6}$ alkyl (optionally substituted by halogen, $C_{1-6}$ alkoxy or phenyl (itself optionally substituted by halogen, $C_{1-4}$ alkyl, $C_{1-4}$ alkoxy or $CF_3$)), $OR^6$, $S(O)_mR^7$, $S(O)_2NR^8R^9$, $NR^{10}S(O)_2R^{11}$, $C(O)R^{12}$, $C(O)NR^{13}R^{14}$, $NR^{15}C(O)R^{16}$, $NR^{17}R^{18}$, $NR^{19}C(O)NR^{20}R^{21}$, methylenedioxy, nitro or cyano;
X is $(CH_2)_n$, where n is 1, 2, 3 or 4;
Y is a 2,4-, 2,5- or 3,5-linking 5-membered heteroaryl ring comprising 2 or 3 heteroatoms independently selected from the group comprising nitrogen, oxygen and sulphur, wherein
Y is optionally substituted by $C_{1-4}$ alkyl;
$R^6$, $R^8$, $R^9$, $R^{10}$, $R^{13}$, $R^{14}$, $R^{15}$, $R^{16}$, $R^{17}$, $R^{18}$, $R^{19}$, $R^{20}$ and $R^{21}$ are, independently, hydrogen or $C_{1-6}$ alkyl (optionally substituted by $C_{1-6}$ alkoxy (provided no acetal or animal is formed) or phenyl (itself optionally substituted by halogen, $C_{1-4}$ alkyl, $C_{1-4}$ alkoxy or $CF_3$));
$R^7$ and $R^{11}$ are, independently, $C_{1-6}$ alkyl (optionally substituted by $C_{1-6}$ alkoxy (provided no thioacetal is formed) or phenyl (itself optionally substituted by halogen, $C_{1-4}$ alkyl, $C_{1-4}$ alkoxy or $CF_3$));
$R^{12}$ is hydrogen, $C_{1-6}$ alkyl (optionally substituted by $C_{1-6}$ alkoxy (provided no acetal is formed) or phenyl (itself optionally substituted by halogen, $C_{1-4}$ alkyl, $C_{1-4}$ alkoxy or $CF_3$)) or $C_{1-6}$ alkoxy (unsubstituted or monosubstituted by $C_{1-6}$ alkoxy or phenyl (itself optionally substituted by halogen, $C_{1-4}$ alkyl, $C_{1-4}$ alkoxy or $CF_3$));
or a pharmaceutically acceptable salt thereof, or solvate thereof, or a solvate of a salt thereof.

Compounds of formula (I) are capable of existing in isomeric forms (for example as tautomers, enantiomers, geometric isomers or diastereomers). The present invention encompasses all such isomers and mixtures thereof in all proportions.

The group Y is a 2,4- or 2,5-linked imidazolyl ring, oxazolyl or thiazolyl ring, a 2,5-linked 1,3,4-oxadiazolyl or 1,3,4-thiadiazolyl ring, or a 3,5-linked isoxazolyl, isothiazolyl, pyrazolyl, 1,2,4-triazolyl, 1,2,4-oxadiazolyl or 1,2,4-thiadiazolyl ring.

Aryl is, for example, phenyl or naphthyl. In one aspect of the invention aryl is phenyl.

Heteroaryl is an aromatic, mono- or bi-cyclic ring system preferably comprising 1, 2 or 3 heteroatoms selected from the group consisting of nitrogen, oxygen and sulphur. Heteroaryl is, for example, imidazolyl, thienyl, furyl, pyrrolyl, pyridinyl, pyrimidinyl, pyrazinyl, pyridazinyl, 1,2,3-, 1,2,4 or 1,3,5-triazinyl, benzo[b]thienyl, benzo[b]furyl, indolyl or quinolinyl. In another aspect of the invention heteroaryl is monocyclic.

Alkyl groups are straight or branched chain and are, for example, methyl, ethyl, n-propyl, iso-propyl, n-butyl, iso-butyl, sec-butyl or tert-butyl. Alkoxy groups are straight or branched chain and are, for example, methoxy, ethoxy, n-propoxy, iso-propoxy or tert-butoxy. Haloalkyl is preferably alkyl optionally substituted with 1, 2 or 3 chloro or fluoro atoms, and is, for example, $CF_3$.

Cycloalkyl is mono- or bi-cyclic and is, for example, cyclopropyl, cyclopentyl, cyclohexyl, bicyclo[2.2.1]heptyl or bicyclo[2.2.2]octyl.

Arylalkyl is, for example, benzyl, 2-phenyleth-1-yl or 1-phenyleth-1-yl. Heteroarylalkyl is, for example, pyridinylmethyl, pyrimidinylmethyl or furylmethyl.

A suitable salt of a compound of formula (I) includes a chloride, bromide, tosylate, mesylate, sulphate or phosphate salt.

In one particular aspect the invention provides a compound of formula (I) wherein: $R^1$ is phenyl which is optionally substituted by halogen, $C_{1-4}$ alkyl, $C_{1-4}$ haloalkyl, $C_{1-4}$ alkoxy, $C_{1-4}$ haloalkoxy, nitro or cyano; $R^2$, $R^3$ and $R^4$ are, independently, hydrogen or $C_{1-4}$ alkyl; $R^5$ is aryl, heteroaryl, aryl(C$_{1-4}$)alkyl or heteroaryl(C$_{1-4}$)alkyl; wherein the aryl and heteroaryl moieties of R$^5$ are optionally substituted by halogen, C$_{1-6}$ alkyl (optionally substituted by halogen, C$_{1-6}$ alkoxy or phenyl (itself optionally substituted by halogen, C$_{1-4}$ alkyl, C$_{1-4}$ alkoxy or CF$_3$)), OR$^6$, S(O)$_m$R$^7$, S(O)$_2$NR$^8$R$^9$, NR$^{10}$S(O)$_2$R$^{11}$, C(O)R$^{12}$, C(O)NR$^{13}$R$^{14}$, R$^{15}$C(O)R$^{16}$, NR$^{17}$R$^{18}$, NR$^{19}$C(O)NR$^{20}$R$^{21}$, methylenedioxy, nitro or cyano; X is (CH$_2$)$_n$, where n is 1, 2, 3 or 4; Y is a 2,4-, 2,5- or 3,5-linking 5-membered heteroaryl ring comprising 2 or 3 heteroatoms independently selected from the group comprising nitrogen, oxygen and sulphur, wherein Y is optionally substituted by C$_{1-4}$ alkyl; R$^6$, R$^8$, R$^9$, R$^{10}$, R$^{13}$, R$^{14}$, R$^{15}$, R$^{16}$, R$^{17}$, R$^{18}$, R$^{19}$, R$^{20}$ and R$^{21}$ are, independently, hydrogen or C$_{1-6}$ alkyl (optionally substituted by C$_{1-6}$ alkoxy (provided no acetal or animal is formed) or phenyl (itself optionally substituted by halogen, C$_{1-4}$ alkyl, C$_{1-4}$ alkoxy or CF$_3$)); R$^7$ and R$^{11}$ are, independently, C$_{1-6}$ alkyl (optionally substituted by C$_{1-6}$ alkoxy (provided no thioacetal is formed) or phenyl (itself optionally substituted by halogen, C$_{1-4}$ alkyl, C$_{1-4}$ alkoxy or CF$_3$)); R$^{12}$ is hydrogen, C$_{1-6}$ alkyl (optionally substituted by C$_{1-6}$ alkoxy (provided no acetal is formed) or phenyl (itself optionally substituted by halogen, C$_{1-4}$ alkyl, C$_{1-4}$ alkoxy or CF$_3$)) or C$_{1-6}$ alkoxy (unsubstituted or mono-substituted by C$_{1-6}$ alkoxy or phenyl (itself optionally substituted by halogen, C$_{1-4}$ alkyl, C$_{1-4}$ alkoxy or CF$_3$)); or a pharmaceutically acceptable salt thereof, or solvate thereof, or a solvate of a salt thereof In a further aspect of the invention n is 2.

In a still further aspect of the invention R$^1$ is phenyl optionally substituted by C$_{1-4}$ alkyl (such as methyl), C$_{1-4}$ alkoxy (such as methoxy) or halogen (such as chloro or fluoro). The group R$^1$ can be phenyl, 4-fluorophenyl, 2,4-difluorophenyl, 2,5-difluorophenyl, 3,4-difluorophenyl, 3,4-dichlorophenyl, 3-fluoro-4-chlorophenyl, 3-fluoro-4-methoxyphenyl or 2-methyl-3-fluorophenyl. The group R$^1$ is, for example, 3,4-dichlorophenyl or 3,4-difluorophenyl.

In yet another aspect of the invention R$^2$ is hydrogen.

In a further aspect of the invention R$^3$ is hydrogen.

In a still further aspect of the invention R$^4$ is hydrogen.

In another aspect of the invention R$^5$ is C$_{1-6}$ alkyl (such as methyl or propyl), C$_{3-8}$ cycloalkyl (such as cyclopropyl, cyclohexyl or bicyclo[2.2.1]heptyl), phenyl, monocyclic heteroaryl, benzyl or monocyclic heteroarylmethyl, wherein the phenyl and heteroaryl moieties of R$^5$ are optionally substituted by halogen (such as chloro or fluoro), C$_{1-4}$ alkyl (such as methyl and iso-propyl), C$_{1-4}$ alkoxy (such as methoxy), C$_{1-4}$ haloalkyl (such as CF$_3$), methylenedioxy, C(O)(C$_{1-4}$ alkyl) (such as acetyl), C$_{1-4}$ thioalkyl (such as SCH$_3$), cyano, N(C$_{1-4}$ alkyl)$_2$ (such as N(CH$_3$)$_2$), NHC(O)(C$_{1-4}$ alkyl) (such as NHC(O)CH$_3$), C(O)N(C$_{1-4}$ alkyl)$_2$ (such as C(O)N(CH$_3$)$_2$) or S(O)$_2$(C$_{1-4}$ alkyl) (such as S(O)$_2$CH$_3$).

In yet another aspect of the invention R$^5$ is phenyl, monocyclic heteroaryl, benzyl or monocyclic heteroarylmethyl, wherein the phenyl and heteroaryl moieties of R$^5$ are optionally substituted by halogen (such as chloro or fluoro), C$_{1-4}$ alkyl (such as methyl and iso-propyl), C$_{1-4}$ alkoxy (such as methoxy), C$_{1-4}$ haloalkyl (such as CF$_3$), methylenedioxy, C(O)(C$_{1-4}$ alkyl) (such as acetyl), C$_{1-4}$ thioalkyl (such as SCH$_3$), cyano, N(C$_{1-4}$ alkyl)$_2$ (such as N(CH$_3$)$_2$), NHC(O)(C$_{1-4}$ alkyl) (such as NHC(O)CH$_3$), C(O)N(C$_{1-4}$ alkyl)$_2$ (such as C(O)N(CH$_3$)$_2$) or S(O)$_2$(C$_{1-4}$ alkyl) (such as S(O)$_2$CH$_3$).

Monocyclic heteroaryl is, for example, pyridinyl, furyl or thiazolyl.

In a further aspect R$^5$ is 2,4-difluorophenyl, 2-pyridyl, 3-pyridyl, 2-fluorophenyl, 2-chlorophenyl or 3-cyanophenyl.

In a still further aspect Y is a 2,5-linked thiazolyl ring (optionally substituted with C$_{1-4}$ alkyl, for example methyl), or a 3,5-linked 1,2,4-triazolyl, 1,2,4-oxadiazolyl, 1,3,4-oxadiazolyl or 1,3,4-thiadiazolyl ring. For example, Y is 3,5-linked 1,2,4-oxadiazolyl or 2,5-linked thiazolyl.

In another aspect the present invention provides a compound of formula (Ia):

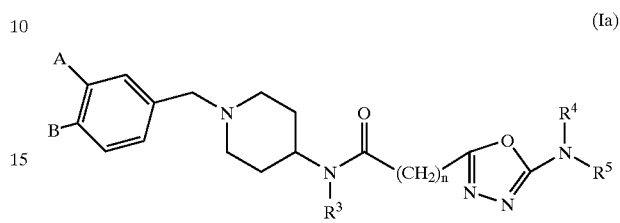

(Ia)

wherein A and B are (for example, independently) chloro or fluoro, and R$^3$, n, R$^4$ and R$^5$ are as defined above.

In yet another aspect the present invention provides a compound of formula (Ia'):

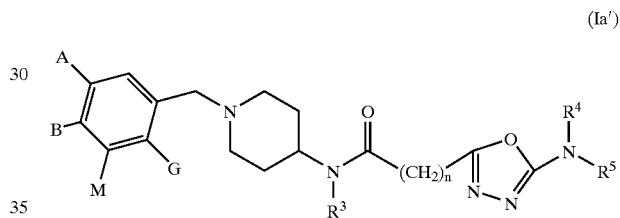

(Ia')

wherein A, B, G and M are, independently, hydrogen, chloro, fluoro, C$_{1-4}$ alkyl (for example methyl) or C$_{1-4}$ alkoxy (for example methoxy), and R$^3$, n, R$^4$ and R$^5$ are as defined above.

In another aspect the present invention provides a compound of formula (Ib):

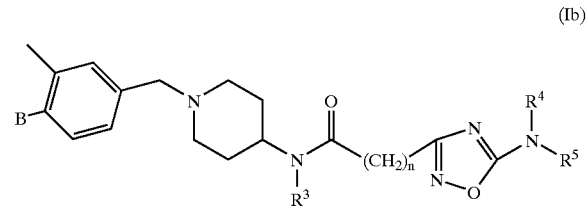

(Ib)

wherein A and B are (for example, independently) chloro or fluoro, and R$^3$, n, R$^4$ and R$^5$ are as defined above.

In yet another aspect the present invention provides a compound of formula (Ib'), wherein A, B, G and M are, independently, hydrogen, chloro, fluoro, C$_{1-4}$ alkyl (for example methyl) or C$_{1-4}$ alkoxy (for example methoxy), and R$^3$, n, R$^4$ and R$^5$ are as defined above.

In another aspect the present invention provides a compound of formula (Ic):

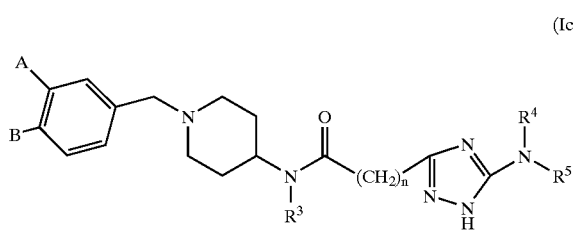

(Ic)

wherein A and B are (for example, independently) chloro or fluoro, and $R^3$, n, $R^4$ and $R^5$ are as defined above.

In yet another aspect the present invention provides a compound of formula (Ic'), wherein A, B, G and M are, independently, hydrogen, chloro, fluoro, $C_{1-4}$ alkyl (for example methyl) or $C_{1-4}$ alkoxy (for example methoxy), and $R^3$, n, $R^4$ and $R^5$ are as defined above.

In another aspect the present invention provides a compound of formula (Id):

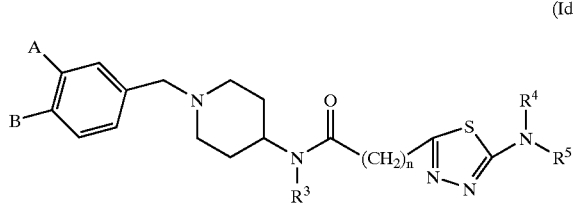

(Id)

wherein A and B are (for example, independently) chloro or fluoro, and $R^3$, n, $R^4$ and $R^5$ are as defined above.

In yet another aspect the present invention provides a compound of formula (Id'), wherein A, B, G and M are, independently, hydrogen, chloro, fluoro, $C_{1-4}$ alkyl (for example methyl) or $C_{1-4}$ alkoxy (for example methoxy), and $R^3$, n, $R^4$ and $R^5$ are as defined above.

In another aspect the present invention provides a compound of formula (Ie):

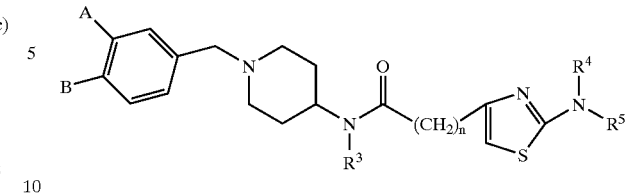

(Ie)

wherein A and B are (for example, independently) chloro or fluoro, and $R^3$, n, $R^4$ and $R^5$ are as defined above.

In yet another aspect the present invention provides a compound of formula (Ie'), wherein A, B, G and M are, independently, hydrogen, chloro, fluoro, $C_{1-4}$ alkyl (for example methyl) or $C_{1-4}$ alkoxy (for example methoxy), and $R^3$, n, $R^4$ and $R^5$ are as defined above.

In another aspect the present invention provides a compound of formula (If):

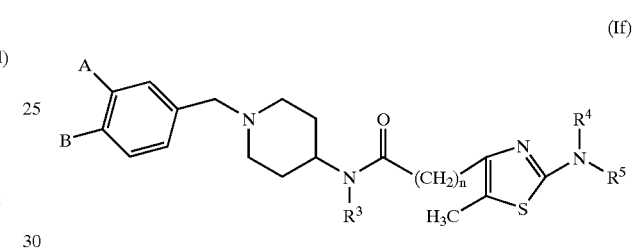

(If)

wherein A and B are (for example, independently) chloro or fluoro, and $R^3$, n, $R^4$ and $R^5$ are as defined above.

In yet another aspect the present invention provides a compound of formula (If'), wherein A, B, G and M are, independently, hydrogen, chloro, fluoro, $C_{1-4}$ alkyl (for example methyl) or $C_{1-4}$ alkoxy (for example methoxy), and $R^3$, n, $R^4$ and $R^5$ are as defined above.

Examples of compounds of the invention are presented in the Tables below.

TABLE I

All compounds in Table I are of formula (Ia'):

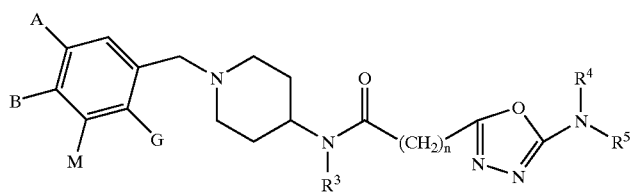

(Ia')

| Compound No. | A | B | G | M | n | $R^3$ | $R^4$ | $R^5$ |
|---|---|---|---|---|---|---|---|---|
| 1 | Cl | Cl | H | H | 1 | H | H | $C_6H_5$ |
| 2 | Cl | Cl | H | H | 1 | H | H | 4-$OCH_3$—$C_6H_4$ |
| 3 | Cl | Cl | H | H | 1 | H | H | 2-$CH_3$—$C_6H_4$ |
| 4 | Cl | Cl | H | H | 1 | H | H | Pyridin-3-yl |
| 5 | Cl | Cl | H | H | 1 | H | H | 2-Cl—$C_6H_4$ |
| 6 | Cl | Cl | H | H | 2 | H | H | 2-Cl—$C_6H_4$ |
| 7 | Cl | Cl | H | H | 2 | H | H | 4-$OCH_3$—$C_6H_4$ |
| 8 | Cl | Cl | H | H | 2 | H | H | 2-$OCH_3$—$C_6H_4$ |
| 9 | Cl | Cl | H | H | 2 | H | H | 3,4-Methylenedioxyphenyl |
| 10 | Cl | Cl | H | H | 2 | H | H | 4-$CH_3$—$C_6H_4$ |
| 11 | Cl | Cl | H | H | 2 | H | H | Pyridin-3-yl |
| 12 | Cl | Cl | H | H | 2 | H | H | 3-Cl—$C_6H_4$ |

TABLE I-continued

All compounds in Table I are of formula (Ia'):

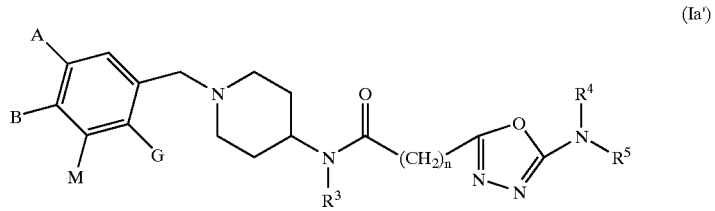

(Ia')

| Compound No. | A | B | G | M | n | R³ | R⁴ | R⁵ |
|---|---|---|---|---|---|---|---|---|
| 13 | F | F | H | H | 2 | H | H | 3-C(O)CH₃—C₆H₄ |
| 14 | F | F | H | H | 2 | H | H | 4-CN—C₆H₄ |
| 15 | F | F | H | H | 2 | H | H | 2,4-F₂—C₆H₃ |
| 16 | F | F | H | H | 2 | H | H | 2-OCH₃—C₆H₄ |
| 17 | F | F | H | H | 2 | H | H | 2,6-F₂—C₆H₃ |
| 18 | F | F | H | H | 2 | H | H | 3-SCH₃—C₆H₄ |
| 19 | F | F | H | H | 2 | H | H | 3-CN—C₆H₄ |
| 20 | F | F | H | H | 2 | H | H | 4-CH₃—C₆H₄ |
| 21 | F | F | H | H | 2 | H | H | 4-Cl—C₆H₄ |
| 22 | F | F | H | H | 2 | H | H | 2-Cl—C₆H₄ |
| 23 | F | F | H | H | 2 | H | H | 2-F—C₆H₄ |
| 24 | F | F | H | H | 2 | H | H | 2-CH₃—C₆H₄ |
| 25 | F | F | H | H | 2 | H | H | 4-N(CH₂CH₃)₂—C₆H₄ |
| 26 | F | F | H | H | 2 | H | H | Pyridin-3-yl |
| 27 | F | F | H | H | 2 | H | H | 3-Cl—C₆H₄ |
| 28 | F | F | H | H | 2 | H | H | 2,4-Cl₂—C₆H₃ |
| 29 | F | F | H | H | 2 | H | H | 4-N(CH₃)₂—CH₄ |
| 30 | F | F | H | H | 2 | H | H | 4-SCH₃—C₆H₄ |
| 31 | F | F | H | H | 2 | H | H | 3,4-Methylenedioxyphenyl |
| 32 | F | F | H | H | 2 | H | H | 4-S(O)₂NH₂—C₆H₄ |
| 33 | F | F | H | H | 2 | H | H | 4-NHC(O)CH₃—C₆H₄ |
| 34 | F | F | H | H | 2 | H | H | 3-NHC(O)CH₃—C₆H₄ |
| 35 | F | F | H | H | 2 | H | H | 3-C(O)N(CH₃)₂—C₆H₄ |
| 36 | F | F | H | H | 2 | H | H | 4-C(O)N(CH₃)₂—C₆H₄ |
| 37 | F | F | H | H | 2 | H | H | Pyridin-2-yl |
| 38 | F | F | H | H | 2 | H | H | 4-S(O)₂CH₃—C₆H₄ |
| 39 | F | F | H | H | 2 | H | H | 3-S(O)₂CH₃—C₆H₄ |
| 40 | F | F | H | H | 2 | H | H | 2,5-F₂—C₆H₃ |
| 41 | F | F | H | H | 2 | H | H | 2-CH(CH₃)₂—C₆H₄ |
| 42 | F | F | H | H | 2 | H | H | 2-CF₃—C₆H₄ |
| 43 | F | F | H | H | 2 | H | H | 2,4,5-F₃—C₆H₂ |
| 44 | F | F | H | H | 2 | H | H | 2-Cl-5-CF₃—C₆H₃ |
| 45 | F | F | H | H | 2 | H | H | 3-F—C₆H₄ |
| 46 | F | F | H | H | 2 | H | H | C₆H₅ |
| 47 | F | F | H | H | 2 | H | H | 2-CH₃-4-F—C₆H₃ |
| 48 | F | F | H | H | 2 | H | H | Thiazol-2-yl |
| 49 | F | F | H | H | 2 | H | CH₃ | 2,4-F₂—C₆H₃ |
| 50 | Cl | Cl | H | H | 2 | H | CH₃ | Pyridin-3-yl |
| 51 | Cl | Cl | H | H | 2 | CH₃ | H | Pyridin-3-yl |
| 52 | F | F | H | H | 2 | H | H | CH₂(pyridin-3-yl) |
| 53 | F | F | H | H | 2 | H | H | CH₂(4-F—C₆H₄) |
| 54 | F | F | H | H | 2 | H | H | CH₂(4-OCH₃—C₆H₄) |
| 55 | F | F | H | H | 2 | H | H | CH₂(fur-2-yl) |
| 56 | F | F | H | H | 2 | H | H | Cyclohexyl |
| 57 | F | F | H | H | 2 | H | H | 2,6-(CH₃)₂—C₆H₃ |
| 58 | F | F | H | H | 2 | H | H | Bicyclo[2.2.1]hept-2-yl |
| 59 | F | F | H | H | 2 | H | H | Cyclopropyl |
| 60 | F | F | H | H | 2 | H | H | Ethyl |
| 61 | F | F | H | H | 2 | H | H | iso-Propyl |
| 62 | F | F | H | H | 2 | H | H | CH₂(2-Cl—C₆H₄) |
| 63 | H | H | H | H | 2 | H | H | 2,4-F₂—C₆H₃ |
| 64 | H | F | H | H | 2 | H | H | 2,4-F₂—C₆H₃ |
| 65 | F | H | F | H | 2 | H | H | 2,4-F₂—C₆H₃ |
| 66 | F | H | H | F | 2 | H | H | 2,4-F₂—C₆H₃ |
| 67 | H | H | CH₃ | F | 2 | H | H | 2,4-F₂—C₆H₃ |
| 68 | F | OCH₃ | H | H | 2 | H | H | 2,4-F₂—C₆H₃ |
| 69 | F | Cl | H | H | 2 | H | H | 2,4-F₂—C₆H₃ |
| 70 | Cl | Cl | H | H | 2 | H | H | 2,4-F₂—C₆H₃ |

TABLE II

Table II comprises 70 compounds of formula (Ib'):

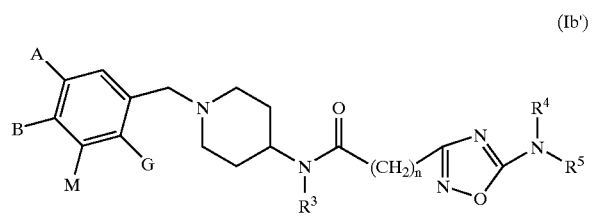

(Ib')

wherein the groups A, B, $R^3$, n, $R^4$ and $R^5$ have the meanings for the correspondingly numbered compound in Table I.

TABLE III

Table III comprises 70 compounds of formula (Ic'):

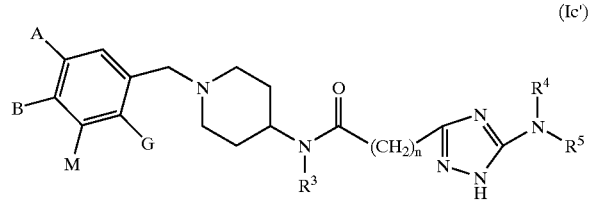

(Ic')

wherein the groups A, B, $R^3$, n, $R^4$ and $R^5$ have the meanings for the correspondingly numbered compound in Table I.

TABLE IV

Table IV comprises 70 compounds of formula (Id'):

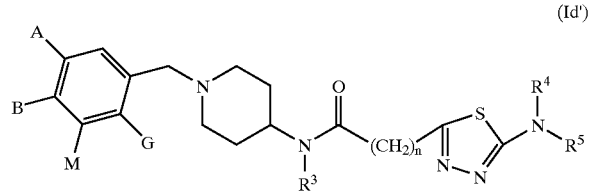

(Id')

wherein the groups A, B, $R^3$, n, $R^4$ and $R^5$ have the meanings for the correspondingly numbered compound in Table I.

TABLE V

Table V comprises 70 compounds of formula (Ie'):

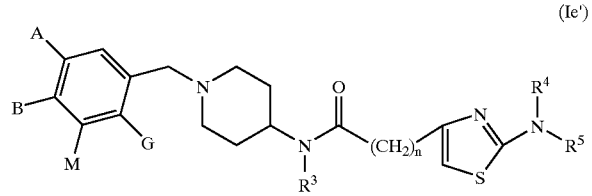

(Ie')

wherein the groups A, B, $R^3$, n, $R^4$ and $R^5$ have the meanings for the correspondingly numbered compound in Table I.

TABLE VI

Table VI comprises 70 compounds of formula (If):

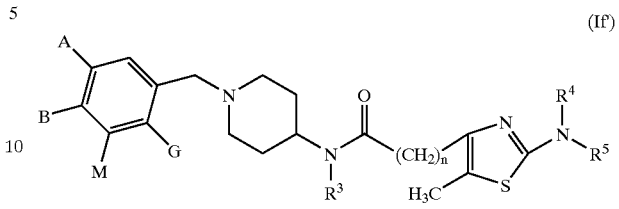

(If)

wherein the groups A, B, $R^3$, n, $R^4$ and $R^5$ have the meanings for the correspondingly numbered compound in Table I.

The compounds of the present invention can be prepared by adaptation of the Examples, by adaptation of methods described in the literature or by one of the methods presented below.

Thus, for example, a compound of formula (I) wherein: Y is oxadiazolyl can be prepared as shown in Schemes 1 and 3 below; Y is 1,2,4-triazolyl can be prepared as shown in Scheme 2 below; Y is oxazole or thiazole can be prepared as shown in Schemes 4 (where Z is oxygen or sulphur), 5, 6, 7 or 11; Y is isoxazole can be prepared as shown in Schemes 8, 9 and 10; Y is pyrazole can be prepared as shown in Scheme 10 (or by using hydrazine in place of hyroxylamine, or the chlorohydrazone in place of the chlorooxime in Schemes 8 and 9); Y is 1,3,4-oxadiazole or thiadiazole can be prepared as shown in Scheme 12; Y is isothiazole can be prepared as shown in Schemes 13 and 14; and Y is 1,2,4-thiadiazole can be prepared as shown in Schemes 15 and 16. Compounds wherein Y is imidazole can be prepared by heating an oxazole with ammonia or an amine, for example in ethanol, if necessary under pressure (for example in a bomb).

In the Schemes:
1. R* is hydrogen or alkyl;
2. in Schemes 8 and 9 Z is a suitably protected or masked acid group such that the acid group does not interfere with the intended reaction. For example it can be an ester or amide, or an alkene (which, on ozonolysis, would generate the acid). The protection and deprotection of functional groups is described in 'Protective Groups in Organic Chemistry', edited by J. W. F. McOmie, Plenum Press (1973) and 'Protective Groups in Organic Synthesis', 3rd edition, T. W. Greene and P. G. M. Wuts, Wiley-Interscience (1999).
3. PyBrOP™ is bromo-tris-pyrrolidino-phosphonium hexafluorophosphate; HATU is O-(7-Azabenzotriazol-1-yl)-N,N,N',N'-tetramethyluronium hexafluorophosphate; HBTU is O-Benzotriazol-1-yl-N,N,N',N'-tetramethyluronium hexafluorophosphate; EDCI is Ethyl dimethylaminopropyl carbodiimide hydrochloride; HOBT is 1-hydroxybenzotriazole; and, DMAP is dimethylaminopyridine
4. RT is room temperature
5. BuLi is a butyl lithium
6. LDA is lithium diisopropylamide
7. A carbodiimide is a coupling agent of the formula —N═C═N—, for example dicyclohexylcarbodiimide or a polymer-bound carbodiimide
8. In Schemes 5, 6, 7, 8, 9, 11, 13, 14 and 15 the final coupling reactions (shown as 'couple') join the final compound with:

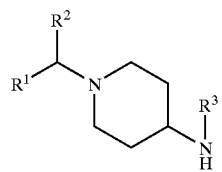

can be carried out following literature methods, for example using PyBrOP™ at room temperature and N,N-dimethylformamide (DMF) as solvent.

9. Curtius reactions can be carried out under literature conditions, for example diphenylphosphoryl azide/base (for example triethylamine or 1,8-bis dimethylaminonaphthalene), then heat, then water to decompose.

The compounds of the invention can be prepared by coupling a compound of formula (II):

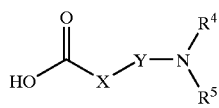

(II)

with a compound of formula (III):

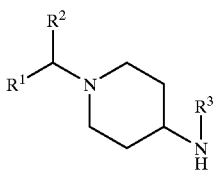

(III)

in the presence of a suitable solvent (such as N,N-dimethylformamide) and in the presence of a suitable coupling agent (for example using PyBrOP™; HATU; HBTU; EDCI/HOBT/DMAP) at a temperature in the range 0–50° C.

A compound of formula (I) wherein $R^2$ is hydrogen can be prepared by reacting a compound of formula (IV):

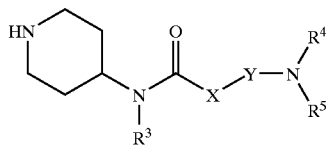

(IV)

with an aldehyde of formula $R^1CHO$ in a suitable solvent (such as N-methylpyrrolidinone) and in the presence of a suitable acid (such as acetic acid); and reducing the product so formed (with, for example, sodium triacetoxyborohydride).

A compound of formula (I) wherein Y is 1,3,4-oxadiazolyl and $R^4$ is hydrogen can be prepared by heating a compound of formula (V):

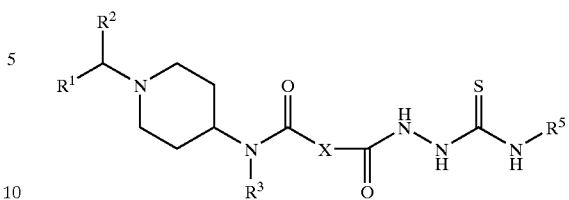

(V)

at a suitable temperature (such as in the range 50–100° C.) in a suitable solvent (such as dimethylformamide and in the presence of a suitable ring-closure chemical (such as N-cyclohexylcarbodiimide, for example supported on a suitable polymer such as polystyrene).

A compound of formula (V) can be prepared by reacting a compound of formula (VI):

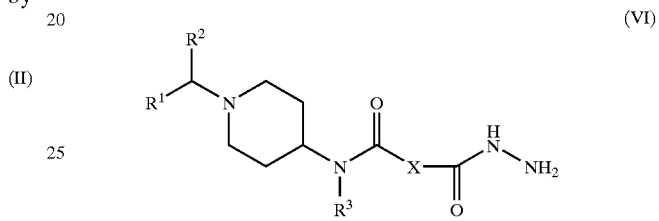

(VI)

with an isothiocyanate of formula $R^5NCS$, in a suitable solvent (such as dimethylformamide) at a temperature in the range 10–40° C.

The starting compounds of all the Schemes are either commercially available, known in the literature or can be prepared using known techniques.

When intermediates in the processes of the present invention contain reactive groups then these may, depending upon the reaction conditions, need to be protected by protecting groups. Thus, the preparation of the compounds of the invention may involve, at an appropriate stage, the addition and subsequent removal of one or more protecting groups.

The compounds of the invention and intermediates may be isolated from their reaction mixtures, and if necessary further purified, by using standard techniques.

In further aspects the present invention provides processes for the preparation of compounds of formula (I), (Ia), (Ia'), (Ib), (Ib'), (Ic), (Ic'), (Id), (Id'), (Ie), (Ie'), (If) and (If').

The compounds of formula (I), (Ia), (Ia'), (Ib), (Ib'), (Ic), (Ic'), (Id), (Id'), (Ie), (Ie'), (If) and (If'), or a salt thereof, a solvate thereof or a solvate of a salt thereof, have activity as pharmaceuticals, in particular as modulators of chemokine receptor activity. More particularly, the compounds have utility as modulators of the activity of chemokine receptor CCR3.

A further aspect of the invention involves the use of a compound of formula (I), (Ia), (Ia'), (Ib), (Ib'), (Ic), (Ic'), (Id), (Id'), (Ie), (Ie'), (If) or (If'), or a salt thereof, a solvate is thereof or a solvate of a salt thereof, in the treatment of conditions or diseases in which modulation of the CCR3 chemoline receptor activity is beneficial.

Thus, the compounds of the invention, or a salt thereof, a solvate thereof or a solvate of a salt thereof, may be used in the treatment of autoimmune, inflammatory, proliferative and hyperproliferative diseases and immunologically-mediated diseases including rejection of transplanted organs or tissues and Acquired Immunodeficiency Syndrome (AIDS). Examples of these conditions include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhitinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, osteoarthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, lichen planus, pemphigus, bullous pemphigus, epidermolysis bullosa, urticaria, angiodermas, vasculitides, eryihemas, cutaneous eosinophilias, uveitis, alopecia areata and vernal conjunctivitis;

(4) (gastrointestinal tract) Coeliac disease, proctitis, eosinopilic gastro-enteritis, mastocytosis, Crohn's disease, inflammatory bowel disease, irritable bowel syndrome, ulcerative colitis, food-related allergies which have effects remote from the gut, e.g., migraine, rhinitis and ezema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura; and (6) (allograft rejection) acute and chronic following, for example, transplantation of kidney, heart, liver, lung, bone marrow, skin and cornea; and chronic graft versus host disease.

Thus, the present invention provides a compound of formula (I), (Ia), (Ia'), (Ib), (Ib'), (Ic), (Ic'), (Id), (Id'), (Ie), (Ie'), (If) or (If'), or a salt thereof, a solvate thereof or a solvate of a salt thereof, as hereinbefore defined for use in therapy; for example in the treatment of a chemokine mediated disease state (especially a CCR3 mediated disease state) in a mammal, such as man, such as in the treatment of a respiratory disease state (for example asthma and/or rhinitis).

The compounds of the invention, or a salt thereof, a solvate thereof or a solvate of a salt thereof, as hereinbefore defined, are especially useful in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}.

In a further aspect, the present invention provides the use of a compound of formula (I), (Ia), (Ia'), (Ib), (Ib'), (Ic), (Ic'), (Id), (Id'), (Ie), (Ie'), (If) or (If'), or a salt thereof, a solvate thereof or a solvate of a salt thereof, as hereinbefore defined in the manufacture of a medicament for use in therapy; for example in the treatment of a chemokine mediated disease state (especially a CCR3 mediated disease state) in a mammal, such as man, such as in the treatment of asthma and/or rhinitis.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention also provides a method of treating a CCR3 mediated disease state (such as an inflammatory disease state) in a mammal (such as man) suffering from, or at risk of, said disease state, which comprises administering to the mammal a therapeutically effective amount of a compound of formula (I), (Ia), (Ia'), (Ib), (Ib'), (Ic), (Ic'), (Id), (Id'), (Ie), (Ie'), (If) or (If'), or a salt thereof, a solvate thereof or a solvate of a salt thereof, as hereinbefore defined.

For the above-mentioned therapeutic uses the dosage administered will, of course, vary with the compound employed, the mode of administration, the treatment desired and the disorder indicated.

A compound of formula (I), (Ia), (Ia'), (Ib), (Ib'), (Ic), (Ic'), (Id), (Id'), (Ie), (Ie'), (If) or (If'), or a salt thereof, a solvate thereof or a solvate of a salt thereof, may be used on its own but will generally be administered in the form of a pharmaceutical composition in which the compound of formula (I), (Ia), (Ia'), (Ib), (Ib'), (Ic), (Ic'), (Id), (Id'), (Ie), (Ie'), (If) or (If'), or a salt thereof, a solvate thereof or a solvate of a salt thereof, (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), (Ia), (Ia'), (Ib), (Ib'), (Ic), (Ic'), (Id), (Id'), (Ie), (Ie'), (If) or (If'), or a salt thereof, a solvate thereof or a solvate of a salt thereof, as hereinbefore defined, in association with a pharmaceutically acceptable adjuvant, diluent or carrier.

The invention further provides a process for the preparation of a pharmaceutical composition of the invention which comprises mixing a compound of formula (I), (Ia), (Ia'), (Ib), (Ib'), (Ic), (Ic'), (Id), (Id'), (Ie), (Ie'), (If) or (If'), or a salt thereof, a solvate thereof or a solvate of a salt thereof, as hereinbefore defined, with a pharmaceutically acceptable adjuvant, diluent or carrier.

The pharmaceutical compositions may be administered topically (for example to is the lung and/or airways or to the skin) in the form of solutions, suspensions, heptafluoroalkane aerosols and dry powder formulations; or systemically, for example by oral administration in the form of tablets, capsules, syrups, powders, aerosols or granules, or by parenteral administration in the form of solutions or suspensions, or by subcutaneous administration or by rectal administration in the form of suppositories or transdermally.

In a further aspect the present invention provides a pharmaceutical combination comprising a compound of formula (I), (Ia), (Ia'), (Ib), (Ib'), (Ic), (Ic'), (Id), (Id'), (Ie), (Ie'), (If) or (If'), or a salt thereof, a solvate thereof or a solvate of a salt thereof, as hereinbefore described, and a histamine antagonist, a steroid, a leukotriene modulator or an IL-5 receptor antibody.

Histamine antagonists include loratidine, desloratidine, fexofenadine, cetirizine, ebastine, astemizole, norastemizole, epinastine or efletirizine.

Steroids include budesonide, fluticasone, mometasone, rofleponide (such as rofleponide palmitate) or formoterol.

Leukotriene modulators include montelukast (such as in its sodium salt form), pranlukast, ZD4407 or zafirlukast The present invention will be further explained by reference to the following illustrative Examples.

EXAMPLE 1

This Example illustrates the preparation of 3-[5-(2-chloro-phenylamino)-[1,3,4]oxadiazol-2-yl]-N-[1-(3,4-dichloro-benzyl)-piperidin-4-yl]-propionamide (Compound No. 6 of Table I).

a) N-[1-(3,4-Dichlorobenzyl)-piperidin-4-yl]-3-hydrazinocarbonyl-propionamide.

A solution of 1-(3,4-dichlorobenzyl)-piperidin-4-ylamine (2.2 g; JP 59101483) and triethylamine (1.53 ml) in dichloromethane (100 ml) stirring at ambient temperature was treated with 3-chlorocarbonyl-propionic acid methyl ester (1.14 ml). After stirring for 16 hours, the reaction mixture was washed with brine, the organic layer was dried (MgSO$_4$), and evaporated to leave a white solid. This solid was suspended in ethanol (100 ml), treated with hydrazine hydrate (5 ml) and the resulting mixture was stirred at reflux for 2 hours and then allowed to cool. Water (30 ml) was added to the reaction mixture and the ethanol was evaporated. The aqueous residue was then extracted into dichloromethane (6×50 ml), the combined organics were dried (MgSO$_4$) and evaporated to give the subtitle compound as a white solid. (1.9 g)

$^1$H NMR (299.98 MHz, CDCl$_3$) 1.38–1.50 (m, 2H), 1.87–1.91 (d, 2H), 2.04–2.15 (m, 2H), 2.44–2.54 (m, 5H), 2.73–2.77 (bd, 2H), 3.41 (s, 2H), 3.63–3.82 (m, 1H), 3,86 (bs, 2H), 5.68–5.71 (bd, 1H), 7.11–7.15 (d, 1H), 7.35–7.38 (d, 1H), 7.41–7.42 (s, 1H).

b) 3-[5-(2-Chloro-phenylamino)-[1,3,4]oxadiazol-2-yl]-N-[1-(3,4-dichloro-benzyl)-piperidin-4-yl]-propionamide 1-Chloro-2-isothiocyanato-benzene (0.112 g) and N-[1-(3,4-dichlorobenzyl)-piperidin-4-yl]-3-hydrazinocarbonyl-propionamide (0.20 g) were stirred together in dimethylformamide (2 ml) at ambient temperature for 2 hours. AM resin (0.324 g, Novabiochem, 2% DVB 1.57 mmol/g) was added and the resulting mixture was stirred at ambient temperature for 16 hours. N-Cyclohexylcarbodiimide N-methyl polystyrene HL (0.638 g, Novabiochem, 1.69 mmol/g) was added and the resulting mixture was stirred at 80° C. for 24 hours, then allowed to cool. The reaction mixture was then filtered, washing with dimethylformamide (2×2 ml). The combined filtrates were evaporated and the residue was purified by reverse phase HPLC to give the title compound as a white solid. (0.028 g, m.pt. 154–156° C., MS [M+H]$^+$ (APCI+) 508/510).

$^1$H NMR (399.98 MHz, DMSO) 1.20–1.42 (m, 2H), 1.60–1.72 (m, 2H), 2.00 (t, 2H), 2.50–2.60 (m, 2H), 2.62–2.72 (m, 2H), 2.93 (t, 2H), 3.41 (s, 2H), 3.41–3.62 (m 1H), 7.06–7.14 (m, 1H), 7.22–7.40 (m, 2H), 7.41–7.61 (m, 3H), 7.81–8.00 (m, 2H), 9.68 (s, 1H).

The following compounds were made from N-[1-(3,4-dichlorobenzyl)-piperidin-4-yl]-3-hydrazinocarbonyl-propionamide and the appropriate isothiocyanate following the method of Example 1 step b).

| Compound No (Table) | m.pt. (° C.) | $^1$H NMR | MS [M + H]$^+$ (APCI+) |
|---|---|---|---|
| 7(I) | 200–213 | (DMSO)1.21–1.48(m, 2H), 1.60–1.78(m, 2H), 2.00(t, 2H), 2.48–2.55(m, 2H), 2.62–2.78(m, 2H), 2.91(t, 2H), 3.42(s, 2H), 3.43–3.61(m, 1H), 3.71(s, 3H), 6.90(d, 2H), 7.27–7.30(m, 1H), 7.43(d, 2H), 7.50–7.60(m, 2H), 7.87(d, 1H), 10.07(s, 1H) | 504/506 |
| 8(I) | 70–82 | (DMSO)1.21–1.48(m, 2H), 1.60–1.78(m, 2H), 2.00(t, 2H), 2.48–2.55(m, 2H), 2.62–2.78(m, 2H), 2.91(t, 2H), 3.42(s, 2H), 3.43–3.61(m, 1H), 3.82(s, 3H), 6.91–7.04(m, 3H), 7.28 (dd, 1H), 7.52–7.60(m, 2H), 7.81–7.95(m, 2H), 9.33(s, 1H) | 504/506 |
| 9(I) | 211–213 | (CDCl$_3$), 1.20–1.60(m, 4H), 1.87–1.90(m, 2H), 2.03–2.18(m, 2H), 2.70–2.80(m, 2H), 3.08(t, 2H), 3.40(s, 2H), 3.78–3.85(m, 1H), 5.74(d, 1H), 5.95(s, 2H), 6.75–6.84(m, 2H), 7.02–7.18 (m, 3H), 7.35–7.41(m, 2H) | 518/520 |
| 10(I) | 105–113 | (CDCl$_3$), 1.20–1.60(m, 4H), 1.82–1.95(m, 2H), 2.03–2.18(m, 2H), 2.31(s, 3H), 2.65–2.80(m, 2H), 3.09(t, 2H), 3.40(s, 2H), 3.71–3.90(m, 1H), 5.74(d, 1H), 7.00(s, 1H), 7.11–7.18(m, 3H), 7.25–7.42(m, 4H) | 488/490 |
| 11(I) | 194–202 | (DMSO)1.32–1.45(m, 2H), 1.62–1.78(m, 2H), 2.02(t, 2H), 2.50–2.59(m, 2H), 2.65–2.75(m, 2H), 2.95(t, 2H), 3.42(s, 2H), 3.43–3.60(m, 1H), 7.22–7.41(m, 2H), 7.45–7.63(m, 2H), 7.90(d, 1H), 8.00(d, 1H), 8.20(d, 1H), 8.69(s, 1H), 10.62(s, 1H) | 476/8 |
| 12(I) | 118–136 | (CDCl$_3$), 1.20–1.60(m, 4H), 1.81–1.98(m, 2H), 2.12(t, 2H), 2.60–2.85(m, 2H), 3.12(m, 2H), 3.40(t, 2H), 3.75–3.90(m, 1H), 5.69(d, 1H), 7.00–7.61(m, 8H) | 508/510 |

-continued

| Compound No (Table) | m.pt. (° C.) | ¹H NMR | MS [M + H]⁺ (APCI+) |
|---|---|---|---|
| 38(I) | 247–248 | (DMSO)1.32–1.45(m, 2H), 1.62–1.78(m, 2H), 2.02(t, 2H), 2.50–2.59(m, 2H), 2.65–2.75(m, 2H), 2.95(t, 2H), 3.18(s, 3H), 3.42(s, 2H), 3.43–3.60(m, 1H), 7.27(d, 1H), 7.50–7.60(m, 2H), 7.72(d, 2H), 7.82–7.93(m, 3H), 10.97 (s, 1H) | 552/4 |
| 39(I) | 214–215 | (DMSO)1.32–1.45(m, 2H), 1.62–1.78(m, 2H), 2.02(t, 2H), 2.50–2.59(m, 2H), 2.65–2.75(m, 2H), 2.95(t, 2H), 3.18(s, 3H), 3.42(s, 2H), 3.43–3.60(m, 1H), 7.20–7.30(m, 1H), 7.43–7.70 (m, 4H), 7.75–7.90(m, 2H), 8.17(s, 1H), 10.81 (s, 1H) | 552/4 |

EXAMPLE 2

The present Example illustrates the preparation of 3-[5-(2-chloro-phenylamino)-[1,3,4]oxadiazol-2-yl]-N-[1-(3,4-difluorobenzyl)-piperidin-4-yl]-propionamide (Compound No. 22 of Table I).

a) N-[1-(3,4-Difluorobenzyl)-piperidinyl]-3-hydrazinocarbonyl-propionamide

A solution of 1-(3,4-difluorobenzyl)-piperidin-4-ylamine (8.7 g; EP-A2-0625507) and triethylamine (7.0 ml) in dichloromethane (200 ml) stirring at ambient temperature was treated with 3-chlorocarbonyl-propionic acid methyl ester (5.2 ml). After stirring for 16 hours, the reaction mixture was washed with brine, the organic layer was dried (MgSO₄), and evaporated to leave a white solid. This solid was suspended in ethanol (200 ml), treated with hydrazine hydrate (5 ml) and the resulting mixture was stirred at reflux for 16 hours and then allowed to cool. Water (30 ml) was added to the reaction mixture and the ethanol was evaporated. The aqueous residue was then extracted into dichloromethane (6×50 ml), the combined organics were dried (MgSO₄) and evaporated to give the subtitle compound as a white solid. (4.8 g)

¹H NMR (399.98 MHz, DMSO) 1.31–1.45 (m, 2H), 1.70 (d, 2H), 2.00 (t, 2H), 2.19–2.37 (m, 4H), 2.72 (d, 2H), 3.42 (s, 2H), 3.43–3.59 (m, 1H), 4.15 (s, 2H), 7.02–7.15 (m, 1H), 7.22–7.41 (m, 2H), 7.76 (d, 1H), 8.94 (s, 1H).

b) 3-[5-(2-Chloro-phenylamino)-[1,3,4]oxadiazol-2-yl]-N-[1-(3,4-difluorobenzyl)-piperidin-4-yl]-propionamide 1-Chloro-2-isothiocyanato-benzene (0.125 g) and N-[1-(3,4-difluorobenzyl)-piperidin-4-yl]-3-hydrazinocarbonyl-propionamide (0.20 g) were stirred together in dimethylformamide (2 ml) at ambient temperature for 2 hours. AM resin (0.35 g, Novabiochem, 2% DVB 1.57 mmol/g) was added and the resulting mixture was stirred at ambient temperature for 16 hours. N-cyclohexylcarbodiimide N-methyl polystyrene HL (0.682 g, Novabiochem, 1.69 mmol/g) was added and the resulting mixture was stirred at 80° C. for 24 hours, then allowed to cool. The reaction mixture was then filtered, washing with dimethylformamide (2×2 ml). The combined filtrates were evaporated and the residue was purified by reverse phase HPLC to give the title compound as a white solid. (0.094 g, m.pt. 162–163° C., MS [M+H]⁺ (APCI+) 476/8).

¹H NMR (399.98 MHz, DMSO) 1.32–1.42 (m, 2H), 1.67–1.74 (m, 2H), 2.00 (t, 2H), 2.50–2.59 (m, 2H), 2.65–2.75 (m, 2H), 2.95 (t, 2H), 3.42 (s, 2H), 3.43–3.60 (m, 1H), 7.05–7.15 (m, 2H), 7.21–7.42 (m, 3H), 7.45 (d, 1H), 7.94 (d, 1H), 7.96 (d, 1H), 9.69 (s, 1H).

The following compounds were made from N-[1-(3,4-difluorobenzyl)-piperidin-4-yl]-3-hydrazinocarbonyl-propionamide and the appropriate isothiocyanate following the method of Example 2 step b).

| Compound No (Table) | m.pt. (° C.) | ¹H NMR | MS [M + H]⁺ (APCI+) |
|---|---|---|---|
| 13(I) | 180–181 | (DMSO)1.20–1.50(m, 2H), 1.78–1.95(m, 2H), 2.00(t, 2H), 2.41–2.51(m, 2H), 2.62–2.73(m, 2H), 2.95(t, 2H), 3.31(s, 3H), 3.42(s, 2H), 3.43–3.59(m, 1H), 7.05–7.10(m, 1H), 7.15–7.30 (m, 2H), 7.48–7.75(m, 2H), 7.85–8.00(m, 2H), 8.08(s, 1H), 10.48(s, 1H) | 484 |
| 14(I) | 246–247 | (DMSO)1.32–1.42(m, 2H), 1.67–1.74(m, 2H), 2.00(t, 2H), 2.50–2.55(m, 2H), 2.64–2.74(m, 2H), 2.95(t, 2H), 3.35(s, 2H), 3.49–3.60(m, 1H), 7.11–7.14(m, 1H), 7.29–7.37(m, 2H), 7.67–7.81(m, 4H), 7.89(d, 1H), 11.00(s, 1H) | 467 |
| 15(I) | 164–165 | (DMSO)1.32–1.42(m, 2H), 1.67–1.74(m, 2H), 2.00(t, 2H), 2.50–2.55(m, 2H), 2.64–2.74(m, 2H), 2.95(t, 2H), 3.35(s, 2H), 3.49–3.60(m, 1H), 7.02–7.18(m, 2H), 7.22–7.40(m, 3H), 7.89(d, 1H), 7.95–8.20(m, 1H), 10.11(s, 1H) | 478 |
| 16(I) | 132–133 | (DMSO)1.32–1.42(m, 2H), 1.67–1.74(m, 2H), 2.00(t, 2H), 2.50–2.55(m, 2H), 2.64–2.74(m, 2H), 2.95(t, 2H), 3.32(s, 2H), 3.49–3.60(m, 1H), 3.82(s, 3H), 6.91–7.08(m, 3H), 7.10–7.18 | 472 |

-continued

| Compound No (Table) | m.pt. (° C.) | ¹H NMR | MS [M + H]⁺ (APCI+) |
|---|---|---|---|
| | | (m, 1H), 7.22–7.41(m, 2H), 7.82–7.92(m, 2H), 9.34(s, 1H) | |
| 17(I) | 198–199 | (DMSO)1.32–1.42(m, 2H), 1.67–1.74(m, 2H), 2.00(t, 2H), 2.50–2.55(m, 2H), 2.64–2.74(m, 2H), 2.95(t, 2H), 3.42(s, 2H), 3.50–3.60(m, 1H), 7.10–7.40(m, 6H), 7.87(d, 1H), 9.70(s, 1H) | 478 |
| 18(I) | 161–162 | (DMSO)1.32–1.42(m, 2H), 1.67–1.74(m, 2H), 2.00(t, 2H), 2.50(s, 3H), 2.51–2.60(m, 2H), 2.65–2.80(m, 2H), 2.95(t, 2H), 3.42(s, 2H), 3.45–3.60(m, 1H), 6.80–6.89(m, 1H), 7.04–7.15 (m, 1H), 7.20–7.40(m, 4H), 7.50(s, 1H), 7.90(d, 1H), 10.38(s, 1H) | 488 |
| 19(I) | 188–189 | (DMSO)1.32–1.42(m, 2H), 1.67–1.74(m, 2H), 2.00(t, 2H), 2.65–2.80(m, 2H), 2.95(t, 2H), 3.18–3.20(m, 2H), 3.42(s, 2H), 3.45–3.60(m, 1H), 7.05–7.15(m, 1H), 7.20–7.60(m, 4H), 7.77(d, 1H), 7.90(d, 1H), 8.00(s, 1H), 10.81 (s, 1H) | 467 |
| 20(I) | 207–208 | (DMSO)1.32–1.42(m, 2H), 1.67–1.74(m, 2H), 2.00(t, 2H), 2.20(s, 3H), 2.51–2.60(m, 2H) 2.65–2.80(m, 2H), 2.95(t, 2H), 3.42(s, 2H), 3.43–3.60(m, 1H), 7.10(d, 3H), 7.25–7.45(m, 4H), 7.90(d, 1H), 10.19(s, 1H) | 456 |
| 21(I) | 199–200 | (DMSO)1.32–1.42(m, 2H), 1.67–1.74(m, 2H), 2.00(t, 2H), 2.50–2.59(m, 2H), 2.65–2.75(m, 2H), 2.95(t, 2H), 3.42(s, 2H), 3.43–3.60(m, 1H), 7.05–7.15(m, 1H), 7.22–7.4(m, 4H), 7.57 (dd, 2H), 7.90(d, 1H), 10.51(s, 1H) | 476/8 |
| 23(I) | 160–161 | (DMSO)1.32–1.42(m, 2H), 1.67–1.74(m, 2H), 2.00(t, 2H), 2.50–2.59(m, 2H), 2.65–2.75(m, 2H), 2.95(t, 2H), 3.42(s, 2H), 3.43–3.60(m, 1H), 7.00–7.40(m, 6H), 7.88(d, 1H), 8.00(t, 1H), 10.13(s, 1H) | 460 |
| 24(I) | 187–189 | (DMSO)1.32–1.42(m, 2H), 1.62–1.75(m, 2H), 2.00(t, 2H), 2.25(s, 3H), 2.50–2.59(m, 2H), 2.65–2.75(m, 2H), 2.95(t, 2H), 3.42(s, 2H), 3.43–3.60(m, 1H), 7.00(t, 1H), 7.08–7.20(m, 3H), 7.24–7.40(m, 2H), 7.70(d, 1H), 7.89(d, 1H), 9.29(s, 1H) | 456 |
| 26(I) | 199–200 | (DMSO)1.32–1.45(m, 2H), 1.62–1.78(m, 2H), 2.02(t, 2H), 2.50–2.59(m, 2H), 2.65–2.75(m, 2H), 2.95(t, 2H), 3.42(s, 2H), 3.43–3.60(m, 1H), 7.10–7.15(m, 1H), 7.22–7.40(m, 3H), 7.90(d, 1H), 8.01(dd, 1H), 8.21(d, 1H), 8.69 (d, 1H), 10.62(s, 1H) | 443 |
| 27(I) | 165–166 | (DMSO)1.32–1.45(m, 2H), 1.62–1.78(m, 2H), 2.00(t, 2H), 2.50–2.59(m, 2H), 2.65–2.75(m, 2H), 2.95(t, 2H), 3.42(s, 2H), 3.43–3.60(m, 1H), 7.00(d, 1H), 7.04–7.15(m, 1H), 7.20–7.45 (m, 4H), 7.69–7.71(m, 1H), 7.88(d, 1H), 10.60 (s, 1H) | 476/8 |
| 28(I) | 154–155 | (DMSO)1.32–1.45(m, 2H), 1.62–1.78(m, 2H), 2.00(t, 2H), 2.50–2.59(m, 2H), 2.65–2.75(m, 2H), 2.95(t, 2H), 3.42(s, 2H), 3.43–3.60(m, 1H), 7.09–7.18(m, 1H), 7.22–7.45(m, 3H), 7.63–7.64(m, 1H), 7.90(d, 1H), 8.00(d, 1H), 9.89(s, 1H) | 510/2 |
| 29(I) | 216–217 | (DMSO)1.32–1.45(m, 2H), 1.62–1.78(m, 2H), 2.00(t, 2H), 2.50–2.59(m, 2H), 2.62–2.75(m, 2H), 2.82(s, 6H), 2.95(t, 2H), 3.42(s, 2H), 3.43–3.60(m, 1H), 6.72–6.74(m, 2H), 7.10–7.15 (m, 1H), 7.25–7.40(m, 4H), 7.88(d, 1H), 9.85(s, 1H) | 485 |
| 30(I) | 213–214 | (DMSO)1.32–1.45(m, 2H), 1.62–1.78(m, 2H), 2.00(t, 2H), 2.45(s, 3H), 2.50–2.59(m, 2H), 2.62–2.75(m, 2H), 2.95(t, 2H), 3.42(s, 2H), 3.43–3.60(m, 1H), 7.10–7.15(m, 1H), 7.20–7.40 (m, 4H), 7.49(d, 2H), 7.90(d, 1H), 10.35 (s,1H) | 488 |
| 31(I) | 202–204 | (DMSO)1.32–1.45(m, 2H), 1.62–1.78(m, 2H), 2.00(t, 2H), 2.50–2.59(m, 2H), 2.62–2.75(m, 2H), 2.95(t, 2H), 3.42(s, 2H), 3.43–3.60(m, 1H), 5.97(s, 2H), 6.85–6.98(m, 2H), 7.15–7.18 (m, 1H), 7.21–7.22(m, 1H), 7.23–7.41(m, 2H), 7.89(d, 1H), 10.18(s, 1H) | 486 |

-continued

| Compound No (Table) | m.pt. (° C.) | ¹H NMR | MS [M + H]⁺ (APCI+) |
|---|---|---|---|
| 33(I) | 236–237 | (DMSO)1.32–1.45(m, 2H), 1.62–1.78(m, 2H), 1.95–2.05(m, 5H), 2.50–2.59(m, 2H), 2.62–2.75 (m, 2H), 2.95(t, 2H), 3.42(s, 2H), 3.43–3.60 (m, 1H), 7.08–7.15(m, 1H), 7.22–7.58(m, 6H), 7.9(d, 1H), 9.84(s, 1H), 10.21(s, 1H) | 499 |
| 34(I) | 215–216 | (DMSO)1.32–1.45(m, 2H), 1.62–1.78(m, 2H), 1.95–2.05(m, 5H), 2.50–2.59(m, 2H), 2.62–2.75 (m, 2H), 2.95(t, 2H), 3.42(s, 2H), 3.43–3.60 (m, 1H), 7.09–7.40(m, 6H), 7.8(s, 1H), 7.90(d, 1H), 9.96(s, 1H), 10.30(s, 1H) | 499 |
| 35(I) | 139–140 | (DMSO)1.32–1.45(m, 2H), 1.62–1.78(m, 2H), 1.95–2.05(m, 2H), 2.50–2.59(m, 2H), 2.62–3.00 (m, 10H), 3.42(s, 2H), 3.43–3.60(m, 1H), 7.00(d, 1H), 7.09–7.45(m, 4H), 7.50–7.62(m, 2H), 7.95(m, 1H), 10.52(s, 1H) | 513 |
| 36(I) | 183–184 | (DMSO)1.32–1.45(m, 2H), 1.62–1.78(m, 2H), 1.95–2.05(m, 2H), 2.50–2.59(m, 2H), 2.62–3.00 (m, 10H), 3.42(s, 2H), 3.43–3.60(m, 1H), 7.10–7.18(m, 1H), 7.30–7.45(m, 4H), 7.60(d, 2H), 7.90(d, 1H), 10.58(s, 1H) | 513 |
| 37(I) | 225–226 | (DMSO)1.32–1.45(m, 2H), 1.62–1.78(m, 2H), 2.02(t, 2H), 2.50–2.59(m, 2H), 2.65–2.75(m, 2H), 2.95(t, 2H), 3.42(s, 2H), 3.43–3.60(m, 1H), 6.87(t, 1H), 7.10–7.15(m, 1H), 7.25–7.41 (m, 3H), 7.65(t, 1H), 7.79(d, 1H), 7.90(d, 1H), 8.20(d, 1H) | 443 |
| 56(I) | | (DMSO)1.41–1.11(m, 6H), 1.57–1.54(m, 1H), 1.70–1.67(m, 4H), 1.90–1.87(m, 2H)2.02–1.97 (m, 2H), 2.45–2.42(m, 2H), 2.72–2.67(m, 2H), 2.83–2.80(m, 2H), 3.27(m, 2H), 3.43(s, 2H), 3.51–3.50(m, 1H), 7.14–7.13(m, 1H), 7.40–7.26 (m, 3H), 7.85–7.83(m, 1H) | 448 |
| 57(I) | | (DMSO)1.41–1.29(m, 2H)1.70–1.66(m, 2H), 2.03–1.96(m, 2H), 2.16(s, 6H), 2.48–2.43(m, 2H under DMSO), 2.73–2.69(m, 2H), 2.89–2.84(m, 2H), 3.43(s, 2H), 3.54–3.50(m, 1H), 7.15–7.09 (m, 4H), 7.41–7.28(m, 2H), 7.86–7.83(d, 1H), 9.05(s, 1H) | 470 |
| 58(I) | | (DMSO)1.14–1.04(m, 3H)1.46–1.24(m, 6H), 1.71–1.60(m, 3H), 2.03–1.96(m, 2H), 2.27–2.20 (m, 3H), 2.46–2.44(m, 2H under DMSO), 2.76–2.69(m, 2H), 2.84–2.79(m, 2H), 3.43(s, 2H), 3.52–3.47(m, 1H), 7.15–7.11(m, 1H), 7.41–7.25 (m, 3H), 7.85–7.83(d, 1H) | 460 |
| 59(I) | | (DMSO)0.48–0.43(m, 2H), 0.68–0.63(m, 2H), 1.43–1.31(m, 2H), 1.71–1.67(m, 2H), 2.03–1.96 (m, 2H), 1.43–1.31(m, 2H), 1.71–1.67(m, 2H), 2.03–1.96(m, 2H), 2.73–2.69(m, 1H), 2.85–2.80 (m, 1H), 3.50(s, 1H), 3.54–3.53(m, 1H), 7.15–7.14(m, 1H), 7.41–7.29(m, 2H), 7.66–7.65 (m, 1H), 7.86–7.84(m, 1H) | 406 |
| 60(I) | | (DMSO)1.14–1.09(t, 3H), 1.43–1.30(m, 2H), 1.71–1.67(m, 2H), 2.03–1.96(m, 2H)2.46–2.41 (m, 2H), 2.73–2.69(m, 2H), 2.4–2.79(m, 2H), 3.19–3.10(m, 2H), 3.43(s, 2H), 3.53–3.49 (m, 1H), 7.15–7.10(m, 1H), 7.41–7.28(m, 3H), 7.86–7.83(m, 1H) | 394 |
| 61(I) | | (DMSO)1.15–1.13(d, 6H), 1.42–1.24(m, 2H), 1.71–1.68(m, 2H), 2.03–1.96(m, 2H), 2.46–2.41 (m, 2H), 2.73–2.69(m, 2H), 2.84–2.79(m, 2H), 3.43(s, 2H), 3.63–3.49(m, 2H), 7.15–7.11 (m, 1H), 7.41–7.22(m, 3H), 7.86–7.83(m, 1H) | 408 |
| 62(I) | | (DMSO)1.61–1.52(m, 2H), 1.95–1.86(m, 2H), 2.57–2.44(m, 2H, under DMSO), 2.90–2.83(m, 2H), 3.12–2.97(m, 2H), 3.37–3.35(m, 2H), 3.77–3.73 (m, 1H), 4.28–4.27(m, 2H), 4.44–4.41(m, 2H), 7.36–7.11(m, 3H), 7.47–7.41(m, 2H)7.65–7.54 (m, 2H), 8.08–7.99(m, 2H) | 490 |

EXAMPLE 3

This Example illustrates the preparation of N-[1-(3,4-Dichlorobenzyl)-piperidin-4-yl]-2-(5-phenylamino-[1,3,4]oxadiazol-2-yl)-acetamide (Compound No. 1 of Table I).

a) N-[1-(3,4-Dichlorobenzyl)-piperidin-4-yl]-2-hydrazinocarbonyl-acetamide

A solution of 1-(3,4-dichlorobenzyl)-piperidin-4-ylamine (2.5 g) and triethylamine (1.50 ml) in dichloromethane (100 ml) stirring at ambient temperature was treated with ethylmalonyl chloride (1.35 ml). After stirring for 16 hours, the reaction mixture was washed with brine, the organic layer was dried (MgSO$_4$), and evaporated to leave a white solid. This solid was suspended in ethanol (100 ml), treated with hydrazine hydrate (5 ml) and the resulting mixture was stirred at reflux for 16 hours and then allowed to cool. Water (100 ml) was added to the reaction mixture and the ethanol was evaporated. The residue was then extracted with dichloromethane (3×100 ml), the combined organics were dried (MgSO$_4$), evaporated. The resultant solid was triturated with diethyl ether to give the subtitle compound as a white solid. (2.27 g)

$^1$HNMR (299.98 MHz, CDCl$_3$) 1.44–1.56 (m, 2H), 1.88–1.92 (d, 2H), 2.10–2.17 (t, 2H), 2.74–2.77 (d, 2H), 3.14 (s, 2H), 3.43 (s, 2H), 3.79–3.81 (m, 1H), 3.91 (bs, 2H), 6.62–6.65 (bd, 1H), 7.13–7.15 (m,1H), 7.36–7.39 (m, 1H), 7.42 (s, 1H), 7.82 (bs, 1H).

b) N-[1-(3,4-Dichlorobenzyl)-piperidin-4-yl]-2-(5-phenylamino-[1,3,4]oxadiazol-2-yl)-acetamide Isothiocyanato-benzene (0.1 ml) and N-[1-(3,4-dichlorobenzyl)-piperidin-4-yl]-2-hydrazinocarbonyl-acetamide (0.10 g) were stirred together in dimethylformamide (2 ml) at ambient temperature for 2 hours. AM resin (0.162 g, Novabiochem, 2% DVB 1.57 mmol/g) was added and the resulting mixture was stirred at ambient temperature for 16 hours. N-cyclohexylcarbodiimide N-methyl polystyrene HL (0.319 g, Novabiochem, 1.69 mmol/g) was added and the resulting mixture was stirred at 80° C. for 24 hours, then allowed to cool. The reaction mixture was then filtered, washing with dimethylformamide (2×2 ml). The combined filtrates were evaporated and the residue was purified by reverse phase HPLC to give the title compound as a white solid. (0.045 g, m.pt 191–217° C., MS [M+H]$^+$ (APCI+) 460/462).

$^1$H NMR (299.98 MHz, DMSO) 1.36–1.52 (m, 2H), 1.63–1.80 (m, 2H), 1.98–2.10 (m, 2H), 270–2.79 (m, 2H), 3.42 (s, 2H), 3.42–3.6 (m, 1H), 3.72 (s, 2H), 6.98 (t, 1H), 7.22–7.35 (m, 3H), 7.43–7.60 (m, 4H), 8.22 (d, 1H).

The following compounds were made from N-[1-(3,4-dichlorobenzyl)-piperidin-4-yl]-2-hydrazinocarbonyl-acetamide and the appropriate isothiocyanate following the method of Example 3 step b).

EXAMPLE 4

This Example illustrates the preparation of 2-(2-Anilino-1,3-thiazol-4-yl)-N-[1-(3,4-dichlorobenzyl)piperidin-4-yl]acetamide (Compound No. 1 of Table V).

2-(2-Anilino-1,3-thiazol-4-yl)-N-[1-(3,4-dichlorobenzyl) piperidin-4-yl]acetamide 1-(3,4-Dichlorobenzyl)-4-piperidinamine (138 mg) was dissolved in dry dichloroethane (2.5 ml) and cooled to −1° C. Trimethylaluminium solution 0.27 ml, 2.0M in hexanes) was added dropwise and the solution was stirred at −1° C. for 10 min and then 30 min at ambient temperature. Ethyl (2-anilino-1,3-thiazol-5-yl)acetate (133 mg) was added and the solution was heated to reflux for 25 h. The reaction was allowed to cool and then ammonium chloride solution (saturated aqueous) was added. The suspension was extracted twice with dichloromethane-methanol and once with dichloromethane. The organic phase was concentrated, then suspended in methanol and filtered. The filtrate was loaded on to an SCX cartridge (International Sorbent Technology Isolute® Flash SCX-2), washed with methanol and then product eluted with 0.7M ammonia in methanol. Reverse phase HPLC (Waters Xterra® Column, eluant 0.5% aqueous ammonia:acetonitrile 75–5:25–95) gave the title compound (27 mg; m.pt. 191–192° C.; MS [M+H]$^+$ (APCI+) 475/477).

$^1$H NMR (399.98 MHz, DMSO) δ 1.43 (qd, 2H), 1.74 (dd, 2H), 2.04 (td, 2H), 2.71 (d, 2H), 3.38 (s, 2H), 3.44 (s, 2H), 3.52–3.62 (m, 1H), 6.54 (s, 1H), 6.92 (t, 1H), 7.24–7.30 (m, 3H), 7.53 (d, 1H), 7.58 (d, 1H), 7.61 (dd, 2H), 7.95 (d, 1H), 10.11 (s, 1H).

EXAMPLE 5

This Example illustrates the preparation of 2-(2-anilino-4-methyl-1,3-thiazol)-4-yl)-N-[1-(3,4-dichlorobenzyl) piperidin-4-yl]acetamide (Compound No. 1 of Table VI).

Prepared from 1-(3,4-dichlorobenzyl)-4-piperidinamine (138 mg) and methyl (2-anilino-5-methyl-1,3-thiazol-4-yl) acetate (141 mg) following the method of Example 4 step (c) followed by recrystallisation from aqueous ethanol to give the title compound (7 mg; m.pt. 172.5–174° C.; MS [M+H]$^+$ (APCI+) 489/491).

| Compound No (Table) | m.pt. (° C.) | $^1$H NMR | MS [M + H]$^+$ (APCI+) |
|---|---|---|---|
| 2(I) | 199–205 | (DMSO)1.37–1.45(m, 2H), 1.72–1.79(m, 2H), 2.00–2.10(m, 2H), 2.70–2.79(m, 2H), 3.32(s, 2H), 3.52–3.6(m, 1H), 3.69(s, 2H), 3.71(s, 3H), 6.91(d, 2H), 7.28(d, 1H), 7.43(d, 2H), 7.53(s, 1H), 7.58(d, 1H), 8.20(d, 1H) | 490/492 |
| 3(I) | 111–118 | (CDCl3)1.4–2.2(m, 7H), 2.32(s, 3H), 2.74–2.80 (m, 2H), 3.42(s, 2H), 3.75(s, 2H), 3.79–3.92 (m, 1H), 6.93(d, 1H), 7.04(t, 1H), 7.1–7.18 (dd, 1H), 7.20(d, 1H), 7.22–7.3(m, 1H), 7.39(d, 1H), 7.41(d, 1H), 7.88(d, 1H) | 474/476 |
| 5(I) | 196–199 | (CDCl3)1.4–2.0(m, 3H), 1.85–1.95(m, 2H), 2.12(t, 2H), 2.70–2.80(m, 2H), 3.43(s, 2H), 3.78(s, 2H), 3.80–3.90(m, 1H), 6.84(d, 1H), 7.02(t, 1H), 7.13(dd, 1H), 7.30–7.42(m, 4H), 8.28(d, 1H) | 494/496 |
| 4(I) | 215–223 | (DMSO)1.32–1.50(m, 2H), 1.65–1.80(m, 2H), 2.02(t, 2H), 2.65–2.75(m, 2H), 3.42(s, 2H), 3.43–3.60(m, 1H), 3.73(s, 2H), 7.29(d, 1H), 7.39–7.41(m, 1H), 7.53(s, 2H), 7.60(d, 1H), 8.00(d, 1H), 8.17–8.28(m, 2H), 8.69(s, 1H) | 461/3 |

¹H NMR (399.98 MHz, DMSO) δ 1.44 (qd, 2H), 1.73 (dd, 2H), 2.04 (td, 2H), 2.21 (s, 3H), 2.71 (d, 2H), 3.29 (s, 2H), 3.44 (s, 2H), 3.51–3.61 (m, 1H), 6.89 (t, 1H), 7.25 (d, 2H), 7.29 (dd, 1H), 7.53 (d, 1H), 7.58 (d, 3H), 7.90 (d, 1H), 9.91 (s, 1H).

EXAMPLE 6

This Example illustrates the preparation of N-[1-(3,4-difluorobenzyl)piperidin-4-yl]-3-{5-[(2,4-difluorophenyl)amino]-1,3,4-thiadiazol-2-yl}propanamide (Compound No. 49 of Table IV).

1-Chloro-2-isothiocyanato-benzene (0.201 g) and N-[1-(3,4-difluorobenzyl)-piperidin-4-yl]-3-hydrazinocarbonyl-propionamide (95 µl) were stirred together in dimethylformamide (2 ml) at ambient temperature for 35 minutes. AM resin (0.35 g, Novabiochem, 2% DVB 1.57 mmol/g) was added and the resulting mixture was stirred at ambient temperature for 135 min. The mixture was filtered and methane sulphonic acid (100 µl) was added and the solution was heated to 110° C. for 4 h. The solvent was evaporated and the residue was partitioned between water and ethyl acetate. The aqueous phase was extracted twice with ethyl acetate; the organic phases were washed with water and then brine, then dried, filtered and evaporated. The residue was loaded on to an SCX cartridge (International Sorbent Technology Isolute® Flash SCX-2), washed with methanol and then product eluted with 0.7M ammonia in methanol. Reverse phase HPLC (Waters Xterra® Column, eluant 0.5% aqueous ammonia:acetonitrile 95–25:5–75; then 60–40:40–60) gave the title compound (3 mg, MS [M+H]⁺ (APCI+) 494).

¹H NMR (399.978 MHz, CDCl₃) δ 1.44 (qd, 3H), 1.87 (d, 2H), 2.09 (td, 3H), 2.69 (t, 3H), 2.71–2.81 (m, 5H), 3.28 (t, 2H), 3.41 (s, 3H), 3.73–3.84 (m, 1H), 5.76 (d, 1H), 6.86–6.93 (m, 2H), 6.96–7.01 (m, 2H), 7.03–7.09 (m, 2H), 7.10–7.18 (m, 2H), 7.95–8.05 (m, 1H).

EXAMPLE 7

This Example illustrates the preparation of N-(1-benzylpiperidin-4-yl)-3-{5-[(2,4-difluorophenyl)amino]-1,3,4-oxadiazol-2-yl} propanamide (Compound No. 63 of Table I).

Step 1: N-[1-benzylpiperidin-4-yl]4-hydrazino-4-oxobutanamide

A solution of 1-(phenylmethyl)-4-piperidinamine, (30 g) and triethylamine (29 ml) in dichloromethane (500 ml) at room temperature was treated dropwise over 20 minutes with 4-chloro-4-oxo-methylbutanoate. The reaction mixture was stirred overnight at room temperature, washed with water and dried (MgSO₄). After evaporation the oily residue was dissolved in ethanol (500 ml), treated with hydrazine hydrate (30 ml) and heated to reflux overnight. After cooling the ethanol was evaporated, the residue was diluted with water and extracted into dichloromethane (4×200 ml), the combined organics were dried (MgSO₄) and evaporated to leave the subtitle compound as a white solid (20 g).

¹H NMR (DMSO-d₆) δ 1.41–1.31(m, 2H), 1.70–1.67(m, 2H), 2.00–1.95 (m, 2H), 2.73–2.67 (m, 4H), 2.95–2.89(m, 2H), 3.42(s, 2H), 3.56–3.50(m, 1H), 7.13–7.08(m, 1H), 7.36–7.21(m, 6H), 7.89–7.87(m, 1H), 8.01–7.87(m, 1H), 10.11(s, 1H)

Step 2: N-(1-benzylpiperidin-4-yl)-3-{5-[(2,4-difluorophenyl)amino]-1,3,4-oxadiazol-2-yl} propanamide Prepared from N-[1-benzylpiperidin-4-yl]-4-hydrazino-4-oxobutanamide following the method of Example 2 step b.

¹H NMR (DMSO-d₆) δ 1.41–1.31(m, 2H), 1.70–1.67(m, 2H), 2.00–1.95(m, 2H), 2.73–2.67(m, 4H), 2.95–2.89(m, 2H), 3.42(s, 2H), 3.56–3.50(m, 1H), 7.13–7.08(m, 1H), 7.36–7.21(m, 6H), 7.89–7.87(m, 1H), 8.01–7.87(m, 1H), 10.11(s, 1H)

MS (APCI +ve) 442, M+H

Step 3: 3-{5-[(2,4-difluorophenyl)amino]-1,3,4-oxadiazol-2-yl}-N-piperidin-4-ylpropanamide N-(1-Benzylpiperidin-4-yl)-3-{5-[(2,4-difluorophenyl)amino]-1,3,4-oxadiazol-2-yl}propanamide (8.14 g, 18.4 mmol) was dissolved in ethanol and hydrogenated over a Pd/C catalyst at 3 bar until the reaction had gone to completion. The reaction mixture was filtered and the filtrate was evaporated to dryness, leaving an off-white solid which was triturated in ether, filtered and then dried in air to leave the subtitle compound (2.68 g, 41%).

¹H NMR (CD₃OD) δ 0.16–0.12(m, 2H), 0.89–0.86(m, 4H), 1.55–1.48(m, 2H), 1.95–1.79(m, 4H), 2.32–2.11(m, 7H), 2.73–2.69(m, 1H), 5.83–5.78(m, 1H), 5.92–5.86(m, 1H), 6.80–6.74(m, 1H)

MS (APCI +ve) 352, M+H

Step 4: N-(1-benzylpiperidin-4-yl)-3-{5-[(2,4-difluorophenyl)amino]-1,3,4-oxadiazol-2-yl}propanamide To a stirred solution of 3-{5-[(2,4-difluorophenyl)amino]-1,3,4-oxadiazol-2-yl}-N-piperidin-4-ylpropanamide (200 mg) in N-methylpyrrolidinone (4 ml) was added benzaldehyde (115 µl) and glacial acetic acid (0.04 ml). The reaction mixture was then heated at 80° C. for 1 hour before being left to cool and sodium triacetoxyborohydride (242 mg) added. The mixture was then stirred at room temperature for 8 hours before being evaporated to dryness and the residue separated into basic and non-basic components using SCX chromatography. Basic fractions were combined and evaporated to dryness. The residue was purified by RPHPLC (MeCN with NH₃ buffer). Fractions containing the desired product were combined and evaporated to dryness to give the title compound. (92 mg).

¹H NMR (DMSO-d₆) δ 1.34–1.27(m, 1H) 1.56–1.43(m, 2H), 1.86–1.77(m, 2H), 2.16–2.08(m, 2H), 2.66–2.62(t, 2H), 2.86–2.81(m, 2H), 3.07–3.03(t, 2H), 3.51(s, 2H), 3.71–6.60 (m, 1H), 7.08–6.93(m, 2H), 7.32–7.31(m, 4H), 7.95–7.93 (m, 1H)

MS (APCI +ve) 442, M+H

The following compounds were made from 3-{5-[(2,4-difluorophenyl)amino]-1,3,4-oxadiazol-2-yl}-N-piperidin-4-ylpropanamide and the appropriate benzaldehyde following the method of Example 7 Step 4.

| Compound No (Table) | ¹H NMR | MS [M + H]⁺ (APCI+) |
|---|---|---|
| 64(I) | DMSO: 1.39–1.31(m, 2H)1.70–1.67(m, 2H), 2.00–1.95 (m, 2H), 2.72–2.66(m, 2H), 2.94–2.91(m, 2H), 3.32–3.29(m, 2H, under DMSO), 3.41(s, 2H), 3.53–3.51 | 460 |

-continued

| Compound No (Table) | $^1$H NMR | MS [M + H]$^+$ (APCI+) |
|---|---|---|
| | (m, 1H), 7.18–7.08(m, 2H), 7.36–7.29(m, 2H), 7.88–7.86(m, 1H), 8.01–7.95(m, 1H), 10.05(s, 1H) | |
| 65(I) | DMSO: 1.42–1.35(m, 2H)7.17–1.68(m, 2H), 2.49–2.02 (m, 2H), 2.6–2.72(m, 2H), 2.95–2.90(m, 2H), 3.32(m, 2H, under DMSO), 3.49(s, 2H), 3.53(m, 1H), 7.26–7.06(m, 3H), 7.36–7.29(m, 1H), 7.89–7.86(m, 1H), 8.00–7.96(m, 1H) | 478 |
| 66(I) | DMSO: 1.43–1.33(m, 2H)1.72–1.68(m, 2H), 2.06–1.98 (m, 2H), 2.73–2.69(m, 2H), 2.95–2.91(m, 2H), 3.32–3.29(m, 2H, under DMSO), 3.47(s, 2H), 3.54–3.51 (m, 1H), 7.12–6.99(m, 4H), 7.36–7.29(m, 1H), 7.89–7.87(m, 1H), 8.02–7.94(m, 1H), 10.09(s, 1H) | 478 |
| 67(I) | DMSO: 1.40–1.24(m, 2H)1.70–1.67(m, 2H), 2.06–2.02 (m, 2H), 2.21(s, 3H), 2.73–2.69(m, 2H), 2.95–2.90 (m, 2H), 3.32–2.95(m, 2H, under DMSO), 3.42(s, 2H), 3.55–3.49(m, 1H), 7.19–7.00(m, 3H), 7.36–7.29 (m, 1H), 7.87–7.85(m, 1H), 8.02–7.94(m, 1H), 10.10(s, 1H) | 474 |
| 68(I) | DMSO: 1.40–1.29(m, 2H)2.00–1.93(m, 2H)2.72–2.69 (m, 2H), 2.95–2.90(m, 2H), 3.32–3.29(m, 2H), 3.36(m, 2H), 3.52–3.50(m, 1H), 3.81(s, 3H), 7.14–7.01 (m, 4H), 7.37–7.29(m, 1H), 7.88–7.85(m, 1H), 8.02–7.94(m, 1H), 10.10(s, 1H) | 490 |
| 69(I) | DMSO: 1.42–1.24(m, 2H)1.71–1.68(m, 2H), 2.05–1.98 (m, 2H), 2.72–2.69(m, 2H), 2.95–2.90(m, 2H), 3.31–3.29(m, 2H, under DMSO), 3.45(s, 2H), 3.54–3.51 (m, 1H), 7.18–7.08(m, 1H), 7.37–7.29(m, 1H), 7.55–7.49(m, 1H), 7.89–7.87(m, 1H), 8.02–7.94(m, 1H), 10.10(s, 1H) | 494 |
| 70(I) | DMSO: 1.42–1.31(m, 2H)1.71–1.68(m, 2H), 2.05–1.98 (m, 2H), 2.73–2.69(m, 2H), 2.95–2.90(m, 2H), 3.31–3.21(m, 2H, under DMSO), 3.44(s, 2H), 3.54–3.51 (m, 1H), 7.13–7.08(m, 1H), 7.37–7.27(m, 2H), 7.59–7.53(m, 2H), 7.89–7.86(m, 1H), 8.02–7.94(m, 1H), 10.10(s, 1H) | 511 |

EXAMPLE 8

Pharmacological Analysis

Calcium Flux $[Ca^{2+}]_i$ Assay a) Human Eosinophils

Human eosinophils were isolated from EDTA anticoagulated peripheral blood as previously described (Hansel et al., *J. Immunol. Methods*, 1991, 145, 105–110). The cells were resuspended (5×10$^6$ ml$^{-1}$) and loaded with 5 µM FLUO-3/AM+Pluronic F127 2.2 µl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at 2.5×10$^6$ ml$^{-1}$. The cells were then transferred to 96 well FLIPR plates (Poly-D-Lysine plates from Becton Dickinson pre-incubated with 5 µM fibronectin for two hours) at 100 ml/well. The plate was centrifuged at 200 g for 5 min and the cells were washed twice with LKS (200 µl; room temperature).

A compound of the Examples was pre-dissolved in dimethylsulphoxide and added to a final concentration of 0.1% (v/v) dimethylsulphoxide. Assays were initiated by the addition of an A$_{50}$ concentration of eotaxin and the transient increase in fluo-3 fluorescence (l$_{Ex}$=490 nm and l$_{Em}$=520 nm) monitored using a FLIPR (Fluorometric Imaging Plate Reader, Molecular Devices, Sunnyvale, U.S.A.).

b) Human Monocytes

Human monocytes were isolated from EDTA anticoagulated peripheral blood as previously described (Cunoosamy & Holbrook, J. Leukocyte Biology, 1998, S2, 13). Cells were resuspended (5×10$^6$ ml$^{-1}$) in LKS and loaded with 5 µM FLUO-3/AM+Pluronic F127 2.2 µl/ml (Molecular Probes) for one hour at room temperature. After loading, cells were centrifuged at 200 g for 5 min and resuspended in LKS at 0.5×10$^6$ ml$^{-1}$. The cells were then transferred to 96 well FLIPR plates (Costar). To each well 100 µl of cells were added at a concentration of 0.5×10$^6$ ml$^{-1}$. The plates were centrifuged (200 g; 5 mins; room temperature) to allow the cells to adhere. After centrifugation the cells were washed twice with LKS (200 µl; room temperature).

A compound of the Examples was pre-dissolved in dimethylsulphoxide and added to a final concentration of 0.1% (v/v) dimethylsulphoxide. Assays were initiated by the addition of an A$_{50}$ concentration of MIP-1α and the transient increase in fluo-3 fluorescence (l$_{Ex}$=490 nm and l$_{Em}$=520 nm) monitored using a FLIPR (Fluorometric Imaging Plate Reader, Molecular Devices, Sunnyvale, U.S.A.).

The compounds of the Examples were found to be antagonists of the eotaxin mediated $[Ca^{2+}]_i$ in human eosinophils and/or antagonists of the MIP-1α mediated $[Ca^{2+}]_i$ in human monocytes.

Human Eosinophil Chemotaxis

Human eosinophils were isolated from EDTA anticoagulated peripheral blood as previously described (Hansel et al., *J. Immunol. Methods*, 1991, 145, 105–110). The cells were resuspended at 10×10$^6$ ml$^{-1}$ in RPMI containing 200 IU/ml penicillin, 200 µg/ml streptomycin sulphate and supplemented with 10% HIFCS, at room temperature.

Eosinophils (700 µl) were pre-incubated for 15 mins at 37° C. with 7 µl of either vehicle or compound (100× required final concentration in 10% dimethylsulphoxide).

The chemotaxis plate (ChemoTx, 3 μm pore, Neuroprobe) was loaded by adding 28 μl of a concentration of eotaxin (0.1 to 100 nM) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% $CO_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton x100 followed by two cycles of freeze/thawing. The cell lysate was then added to the supernatant. The number of eosinophils migrating was quantified according to the method of Strath et al., *J. Immunol. Methods*, 1985, 83, 209 by measuring eosinophil peroxidase activity in the supernatant.

Certain compounds of the Examples were found to be antagonists of the eotaxin mediated human eosinophil chemotaxis.

Scheme 1

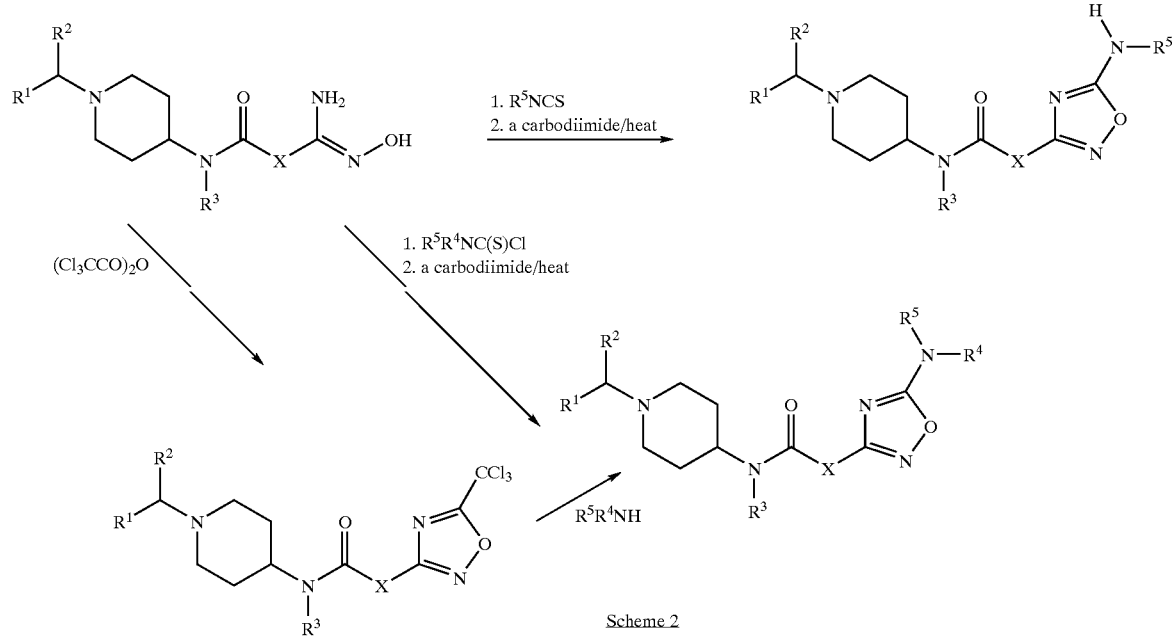

Scheme 2

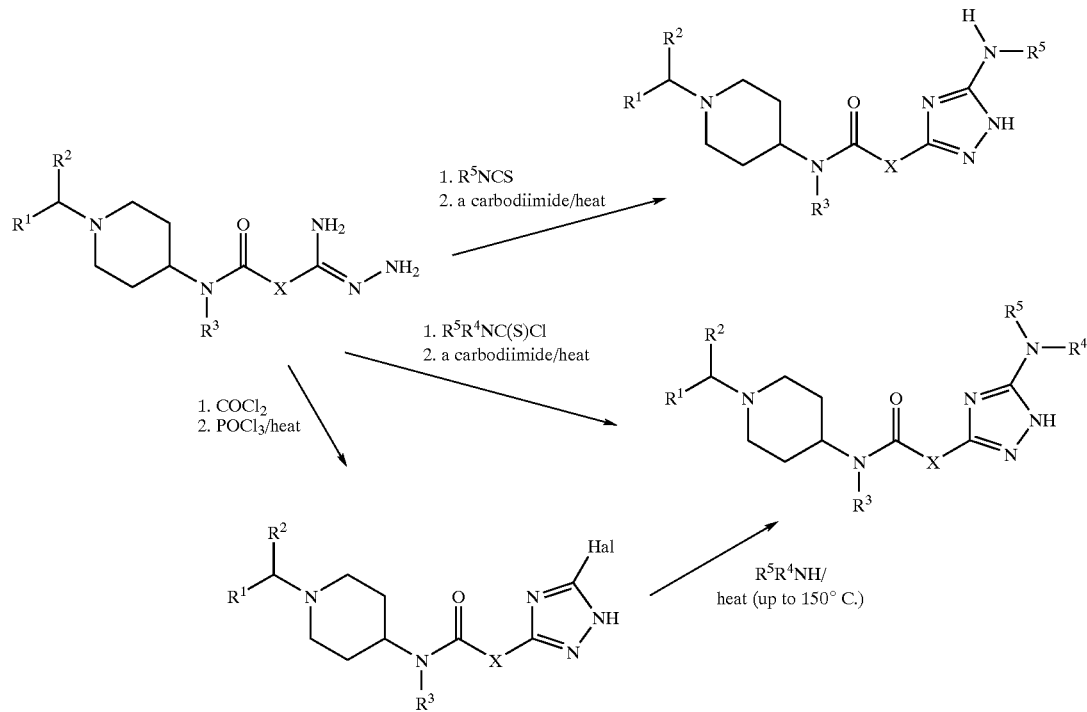

Scheme 3
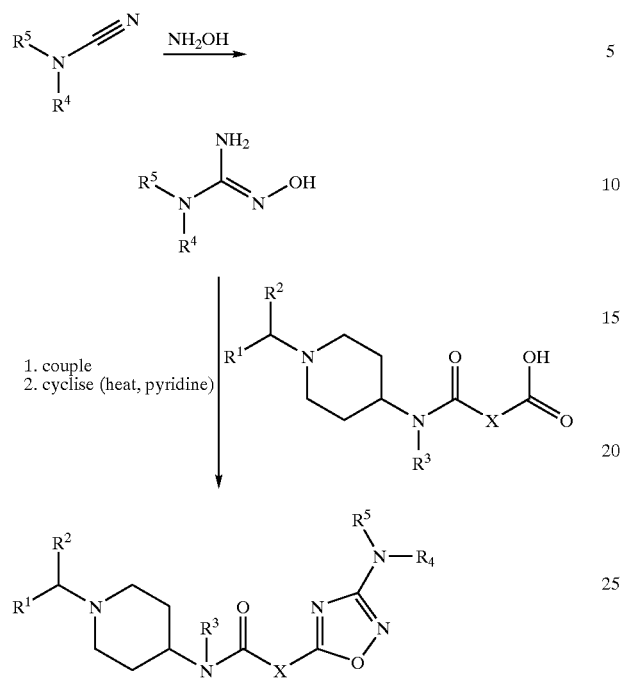
Scheme 4
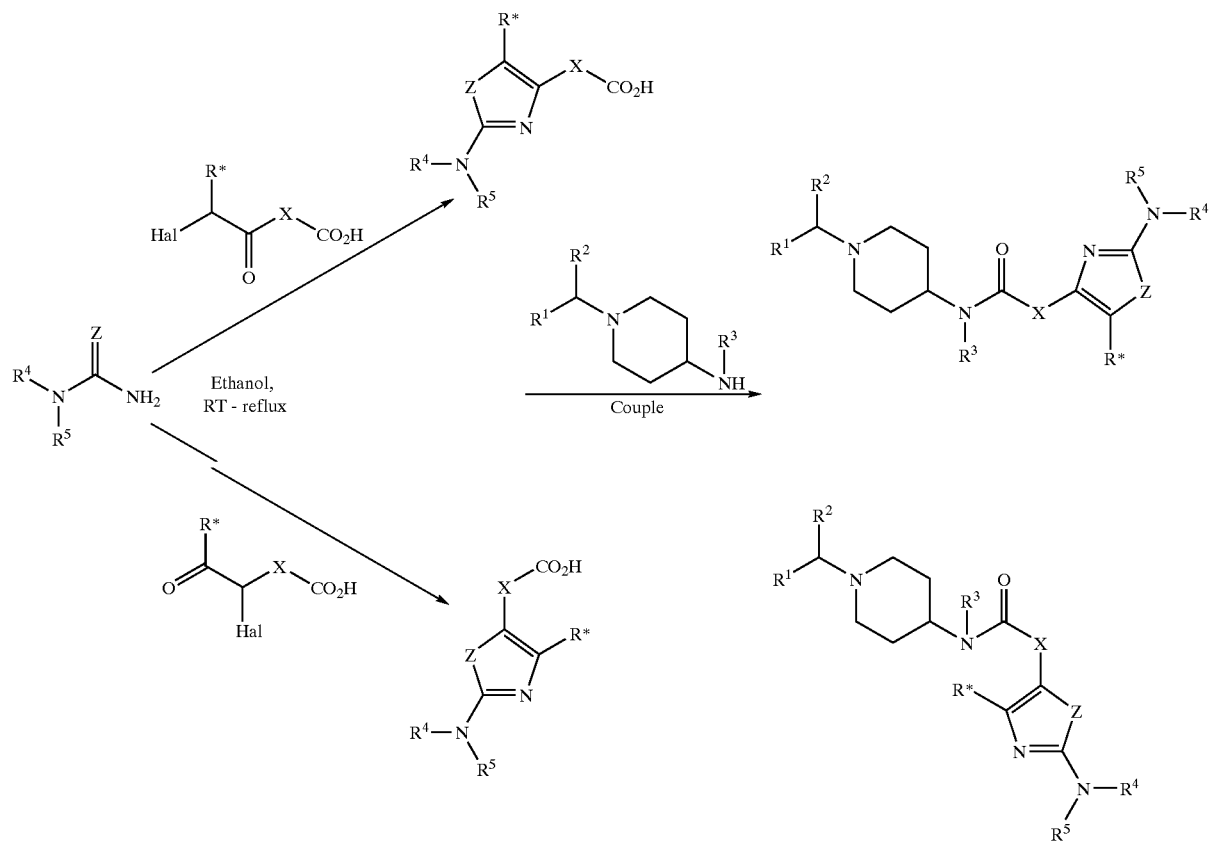

Scheme 5

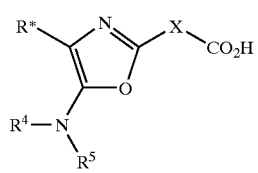

POCl₃/R⁵R⁴NH
CHCl₃/RT to reflux →

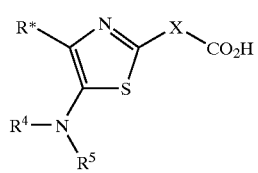

couple →

Scheme 6

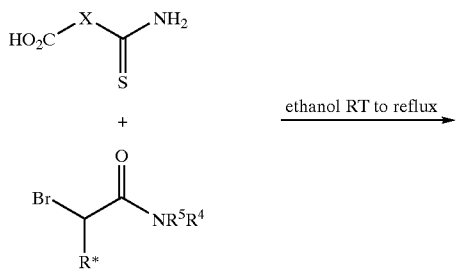

Lawesson's reagent
pyridine, 100° C. →

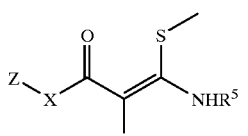

couple →

Scheme 7

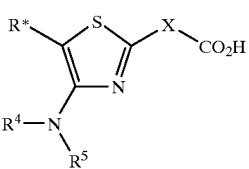

ethanol RT to reflux →

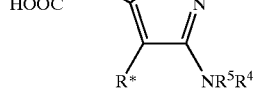

couple →

Scheme 8

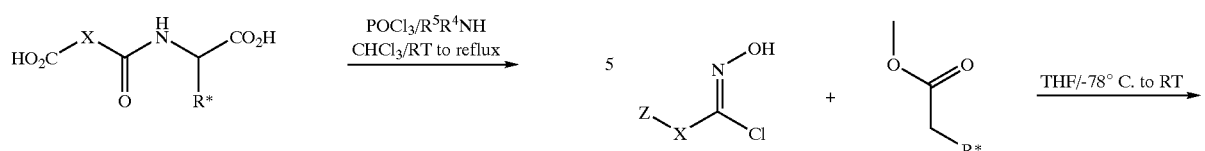

THF/−78° C. to RT →

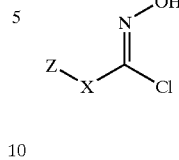

enolate (2 equivalents)

POCl₃/heat →

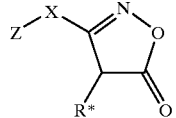

1. R⁵R⁴NLi (from R⁵R⁴NH + BuLi in THF)/THF 0° C. to RT
2. Regenerate acid
→

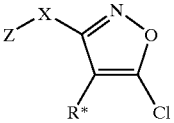

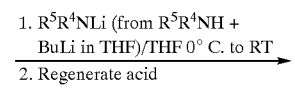

couple →

Scheme 9

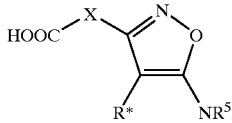

1. Lithiate, eg LDA/THF −78° C.
2. R⁵NCS
3. Methyl iodide
→

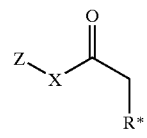

NH₂OH/EtOH →

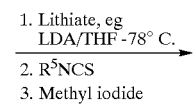

1. R⁴Hal/Base eg NaH/DMF
2. Regenerate acid
→

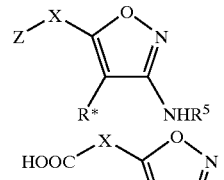

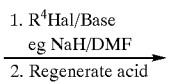

couple →

Scheme 10
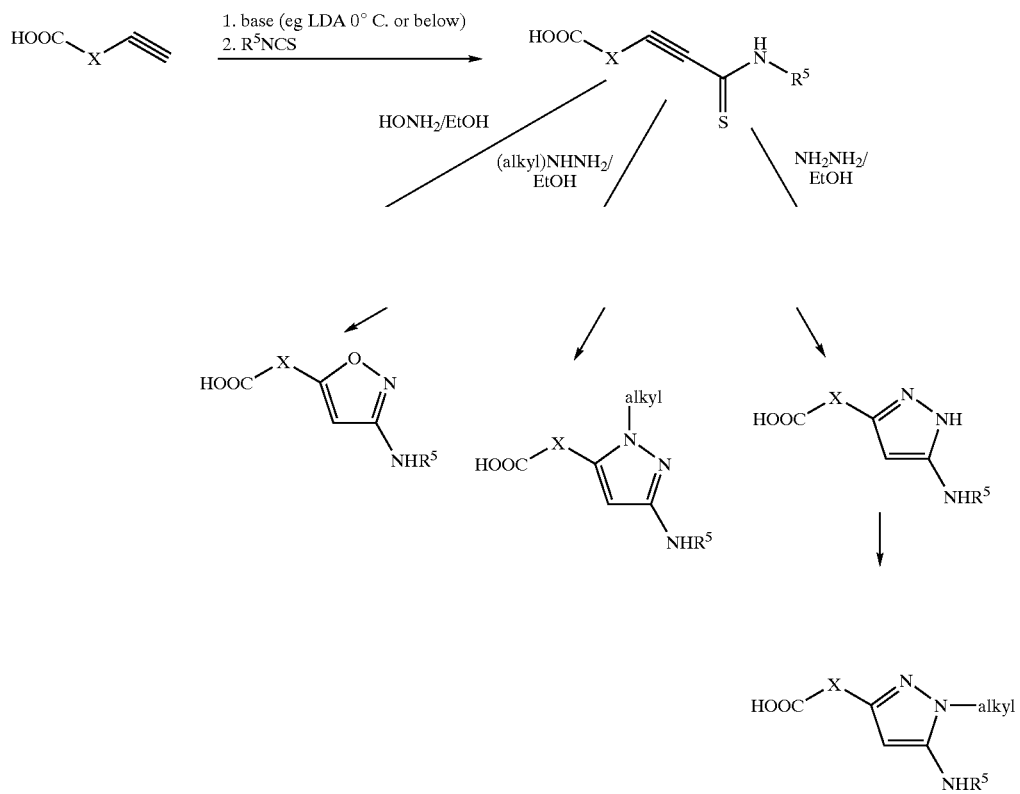
Scheme 11
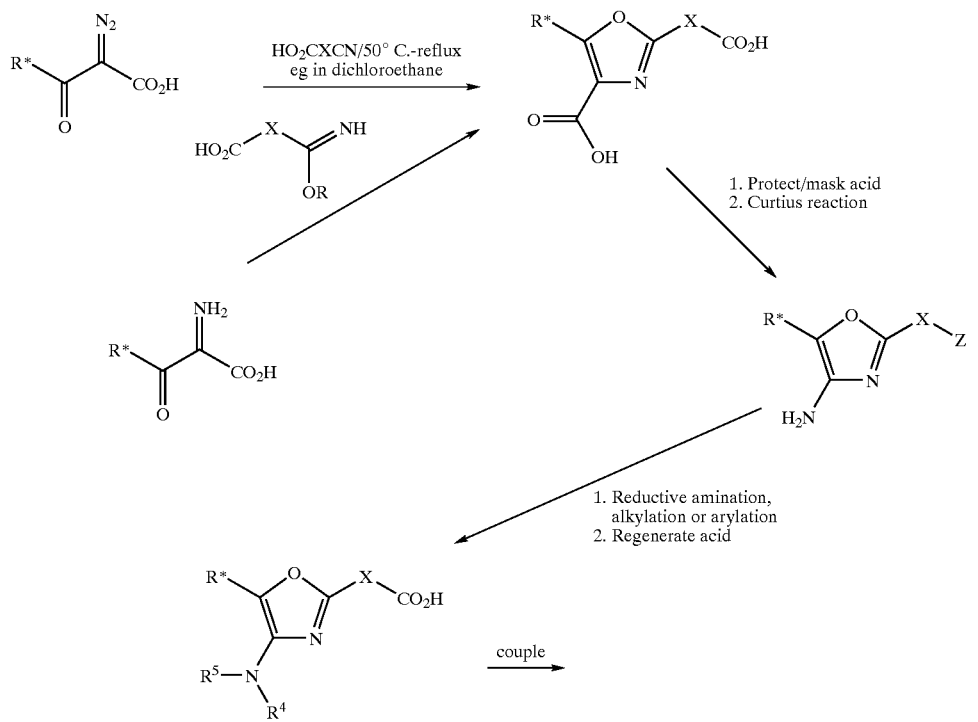

Scheme 12
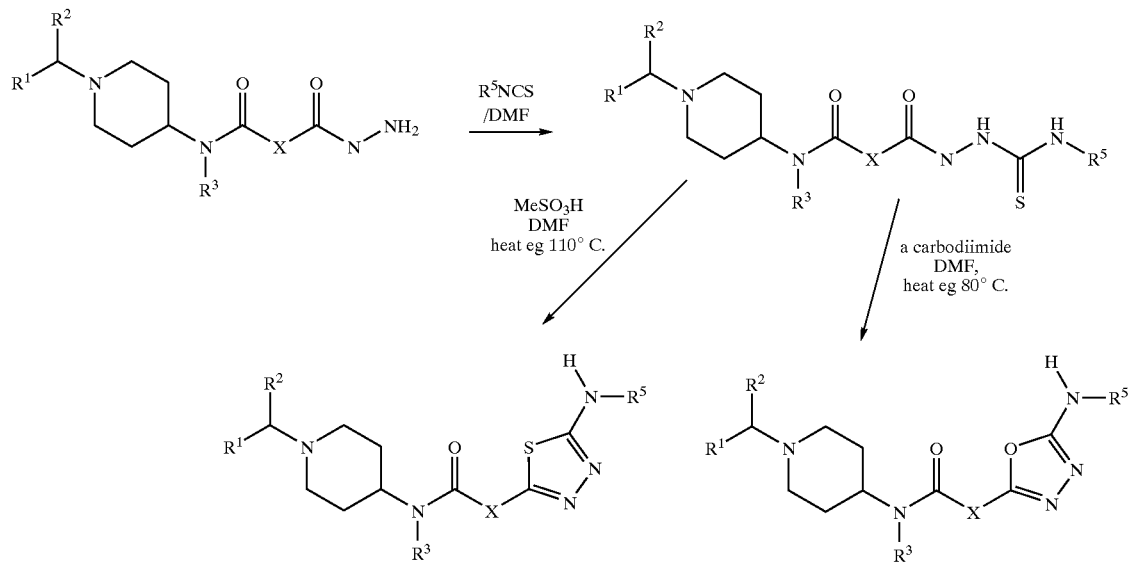
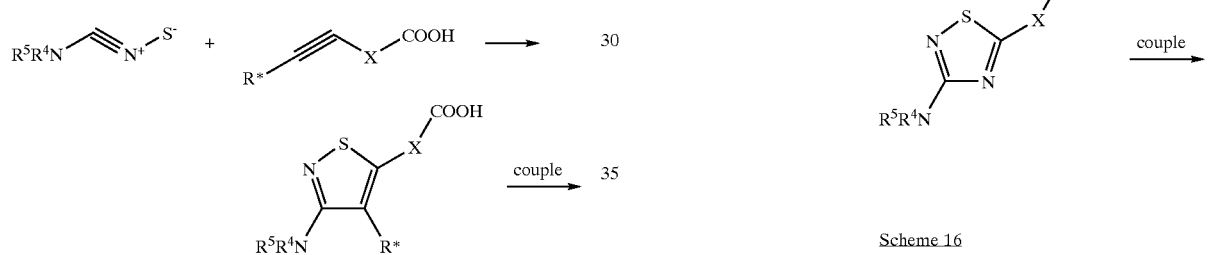
Scheme 16
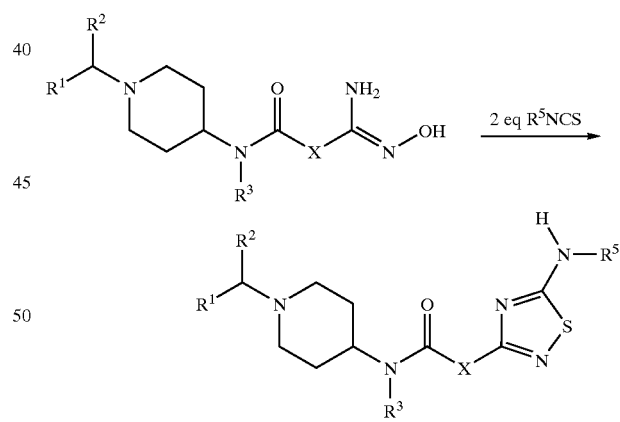
-continued
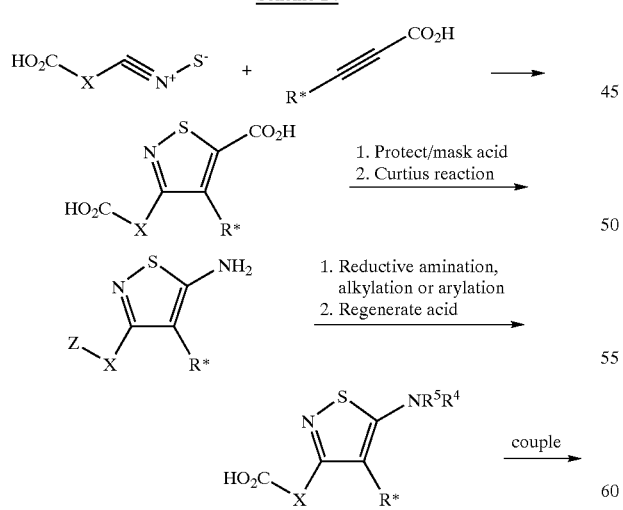
Scheme 15
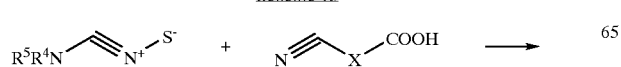
What is claimed is:
1. A compound of formula (I):
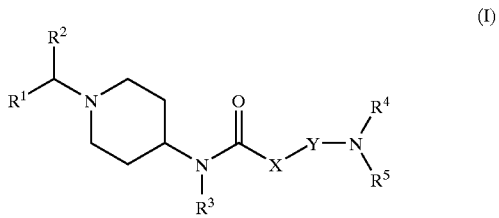

wherein:
R$^1$ is phenyl which is optionally substituted by halogen, C$_{1-4}$ alkyl, C$_{1-4}$ haloalkyl, C$_{1-4}$ alkoxy, C$_{1-4}$ haloalkoxy, nitro or cyano;
R$^2$, R$^3$ and R$^4$ are, independently, hydrogen or C$_{1-4}$ alkyl;
R$^5$ is C$_{1-6}$ alkyl, aryl, heteroaryl, aryl(C$_{1-4}$)alkyl, heteroaryl(C$_{1-4}$)alkyl or C$_{3-8}$ cycloalkyl;
wherein the aryl and heteroaryl moieties of R$^5$ are optionally substituted by halogen, C$_{1-6}$ alkyl (optionally substituted by halogen, C$_{1-6}$ alkoxy or phenyl (itself optionally substituted by halogen, C$_{1-4}$ alkyl, C$_{1-4}$ alkoxy or CF$_3$)), OR$^6$, S(O)$_m$R$^7$, S(O)$_2$NR$^8$R$^9$, NR$^{10}$S(O)$_2$R$^{11}$, C(O)R$^{12}$, C(O)NR$^{13}$R$^{14}$, NR$^{15}$C(O)R$^{16}$, NR$^{17}$R$^{18}$, NR$^{19}$C(O)NR$^{20}$R$^{21}$, methylenedioxy, nitro or cyano;
X is (CH$_2$)$_n$, where n is 1, 2, 3 or 4;
Y is a 2,4-, 2,5- or 3,5-linking 5-membered heteroaryl ring having 2 or 3 heteroatoms independently selected from the group consisting of nitrogen, oxygen and sulphur, wherein Y is optionally substituted by C$_{1-4}$ alkyl;
R$^6$, R$^8$, R$^9$, R$^{10}$, R$^{13}$, R$^{14}$, R$^{15}$, R$^{16}$, R$^{17}$, R$^{18}$, R$^{19}$, R$^{20}$ and R$^{21}$ are independently, hydrogen or C$_{1-6}$ alkyl (optionally substituted by C$_{1-6}$ alkoxy (provided no acetal or aminal is formed) or phenyl (itself optionally substituted by halogen, C$_{1-4}$ alkyl, C$_{1-4}$ alkoxy or CF$_3$));
R$^7$ and R$^{11}$ are, independently, C$_{1-6}$ alkyl (optionally substituted by C$_{1-6}$ alkoxy (provided no thioacetal is formed) or phenyl (itself optionally substituted by halogen, C$_{1-4}$ alkyl, —C$_{1-4}$ alkoxy or CF$_3$));
R$^{12}$ is hydrogen, C$_{1-6}$ alkyl (optionally substituted by C$_{1-6}$ alkoxy (provided no acetal is formed) or phenyl (itself optionally substituted by halogen, C$_{1-4}$ alkyl, C$_{1-4}$ alkoxy or CF$_3$)) or C$_{1-6}$ alkoxy (unsubstituted or monosubstituted by C$_{1-6}$ alkoxy or phenyl (itself optionally substituted by halogen, C$_{1-4}$ alkyl, C$_{1-4}$ alkoxy or CF$_3$));
or a pharmaceutically acceptable salt thereof.

2. A compound as claimed in claim 1 wherein R$^1$ is phenyl optionally substituted by C$_{1-4}$ alkyl, C$_{1-4}$ alkoxy or halogen.

3. A compound as claimed in claim 1 wherein R$^2$, R$^3$ and R$^4$ are all hydrogen.

4. A compound as claimed in claim 1 wherein R$^5$ is C$_{1-6}$ alkyl, C$_{3-8}$ cycloalkyl, phenyl, monocyclic heteroaryl, benzyl or monocyclic heteroarylmethyl, wherein the phenyl and heteroaryl moieties of R$^5$ are optionally substituted by halogen, C$_{1-4}$ alkyl, C$_{1-4}$ alkoxy, C$_{1-4}$ haloalkyl, methylenedioxy, C(O)(C$_{1-4}$ alkyl), C$_{1-4}$ thioalkyl, cyano, N(C$_{1-4}$ alkyl)$_2$, NHC(O)(C$_{1-4}$ alkyl), C(O)N(C$_{1-4}$ alkyl)$_2$ or S(O)$_2$(C$_{1-4}$ alkyl).

5. A compound as claimed in claim 1 wherein X is (CH$_2$)$_2$.

6. A compound as claimed in claim 1 wherein Y is 2,5-linked thiazolyl ring (optionally substituted with C$_{1-4}$ alkyl), or a 3,5-linked 1,2,4-triazolyl, 1,2,4-oxadiazolyl, 1,3,4-oxadiazolyl or 1,3,4-thiadiazolyl ring.

7. A pharmaceutical composition comprising a compound of formula (I), or a pharmaceutically acceptable salt thereof, as claimed in claim 1, and a pharmaceutically acceptable diluent or carrier therefor.

8. A process for preparing a compound as claimed in claim 1 which comprises:

A. coupling a compound of formula (II):

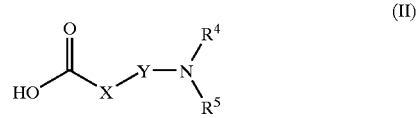

(II)

with a compound of formula (III):

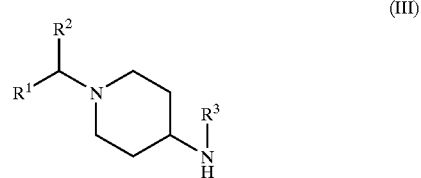

(III)

in a suitable solvent, in the presence of a suitable coupling agent and at a temperature in the range 0–50° C.; or, B. where R$^2$ is hydrogen, reacting a compound of formula (IV):

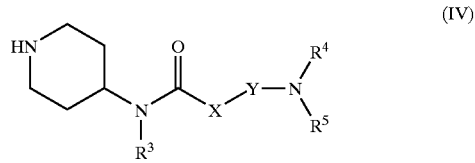

(IV)

with an aldehyde of formula R$^1$CHO in a suitable solvent and in the presence of a suitable acid; and reducing the product so formed; or, C. where Y is 1,3,4-oxadiazolyl and R$^4$ is hydrogen, heating a compound of formula (V):

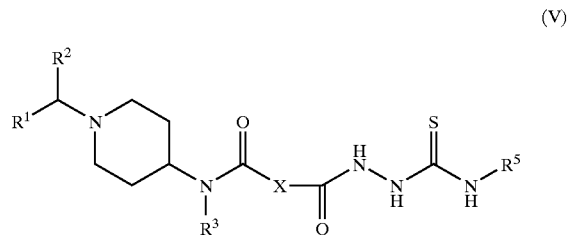

(V)

at a suitable temperature, in a suitable solvent and in the presence of a suitable ring-closure chemical.

* * * * *